United States Patent
Miller, Jr. et al.

(10) Patent No.: US 9,951,102 B2
(45) Date of Patent: Apr. 24, 2018

(54) PEPTIDE INHIBITOR OF NOX1 NADPH OXIDASE

(71) Applicant: University of Iowa Research Foundation, Iowa City, IA (US)

(72) Inventors: Francis J. Miller, Jr., Coralville, IA (US); Jennifer Streeter, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days. days.

(21) Appl. No.: 14/689,803

(22) Filed: Apr. 17, 2015

(65) Prior Publication Data

US 2015/0368301 A1    Dec. 24, 2015

Related U.S. Application Data

(60) Provisional application No. 62/013,916, filed on Jun. 18, 2014.

(51) Int. Cl.
*C07K 7/06* (2006.01)
*C07K 7/08* (2006.01)
*A61K 38/00* (2006.01)

(52) U.S. Cl.
CPC ............ *C07K 7/06* (2013.01); *A61K 38/00* (2013.01); *C07K 2319/01* (2013.01); *C07K 2319/09* (2013.01); *C07K 2319/50* (2013.01)

(58) Field of Classification Search
None
See application file for complete search history.

(56) References Cited

U.S. PATENT DOCUMENTS 6,620,603 B1 *  9/2003  Lambeth ................ C07K 16/40
                                                    435/189

FOREIGN PATENT DOCUMENTS

| WO | WO-0117533 A1    | 5/2001  |
|----|------------------|---------|
| WO | WO-2010138555 A2 | 12/2010 |
| WO | WO-2013074816 A2 | 5/2013  |

OTHER PUBLICATIONS

ThermoFisher Scientific,Nox1 antibody product information sheet, accessed Jul. 10, 2017 at URL thermofisher.com/1/3/nadh-nadph-mitogenic-oxidase-subunit-p65-mox, 1 page.*
Kuroda et al., "The superoxide-producing NAD(P)H oxidase Nox4 in the nucleus of human vascular endothelial cells," Genes to Cells 10:1139-1151 (2005).*
Suh et al., "Cell transformation by the superoxide generating oxidase Mox1," Nature 401:79-82 (1999).*
GST Gene Fusion System (GE Healthcare, Data file 28/9622-84 AA, pp. 1-8 (2009).*
Dassie, Justin P, et al., "Systemic administration of optimized aptamer-siRNA chimeras promotes regression of PSMA-expressing tumors", Journal of Nature Biotechnology 27(9), (Sep. 2009), 839-849.
Hernandez, Luiza I, et al., "Methods for Evaluating Cell-Specific, Cell-Internalizing RNA Aptamers", Journal of Pharmaceuticals (6), (2013), 295-319.
Rockey, William M, et al., "Rational Truncation of an RNA Aptamer to Prostate-Specific Membrane Antigen Using Computational Structural Modeling", The Journal of Nucleic Acid Therapeutics 21(5), (2011), 299-314.
Thiel, Kristina W, et al., "Intracellular delivery of RNA-based therapeutics using aptamers," Therapeutic Delivery 1(6), (Dec. 1, 2010). 849-861.
Thiel, William H, et al., "Rapid identification of Cell-Specific, Internalizing RNA Aptamers with Bioinformatics Analyses of a Cell-Based Aptamer Selectrion", Journal of PLOS one 7(9), (Sep. 2012), 1-14.

* cited by examiner

*Primary Examiner* — Julie Ha
*Assistant Examiner* — Kristina M Hellman
(74) *Attorney, Agent, or Firm* — Schwegman Lundberg & Woessner, P.A.

(57) ABSTRACT

An isolated peptide or fusion having the peptide useful to interfere with the phosphorylation of Nox1, block or inhibit binding of NoxA1 activation domain (AD) to Nox1, and/or prevent or inhibit assembly of the p47phox/NoxA1 complex with Nox1, or a vector encoding the peptide or fusion thereof, and methods of using the peptide, fusion or vector are provided.

11 Claims, 12 Drawing Sheets
(7 of 12 Drawing Sheet(s) Filed in Color)

| Nox1 Site | Predicted Kinase | Score |
|---|---|---|
| T-317 | PKB | 0.87 |
| T-496 | PKC | 0.83 |
| T-429 | PKC | 0.78 |
| T-89 | PKC | 0.76 |
| S-139 | PKC | 0.76 |
| T-170 | PKC | 0.76 |
| S-503 | PKC | 0.73 |
| S-136 | PKA | 0.72 |
| S-415 | PKC | 0.71 |
| S-547 | PKA | 0.7 |
| S-127 | PKA | 0.68 |
| S-548 | PKA | 0.68 |
| S-56 | PKA | 0.66 |
| T-518 | PKC | 0.66 |
| S-538 | PKC | 0.64 |
| S-255 | PKC | 0.63 |
| S-548 | PKC | 0.63 |
| S-77 | PKC | 0.61 |
| S-129 | DNAPK | 0.61 |
| S-136 | DNAPK | 0.61 |
| T-176 | PKC | 0.61 |
| T-340 | CKI | 0.61 |
| S-171 | PKA | 0.6 |
| S-258 | P38MAPK | 0.6 |

FIG. 10

SEQUENCE LISTING

<160> NUMBER OF SEQ ID NOS: 21

<210> SEQ ID NO 1
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 1
gctcattttg caaccacgcg ctgagaaagc cattg          35

<210> SEQ ID NO 2
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 2
caatcccttt ctcagcgcgt ggttgcaaaa tgagc                    35

<210> SEQ ID NO 3
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 3
cgtgcacaca acaagctgaa agcacaaaag atctatttct ac            42

<210> SEQ ID NO 4
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 4
gtagaaatag atcttttgtg ctttcagctt gttgtgtgca cg            42

<210> SEQ ID NO 5
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 5
cgtgcacaca acaagctgaa agaccaaaag atctatttct ac            42

<210> SEQ ID NO 6
<211> LENGTH: 42
<212> TYPE: DNA
<213> ORGANISM: Artificial Sequence
<220> FEATURE:
<223> OTHER INFORMATION: A synthetic oligonucleotide

<400> SEQUENCE: 6
gtagaaatag atcttttggt ctttcagctt gttgtgtgca cg            42

<210> SEQ ID NO 7
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 7
gaattccctg gaacaagaga tggacgaatt aggcaa                   36

<210> SEQ ID NO 8
<211> LENGTH: 65
<212> TYPE: DNA
<213> ORGANISM: Artificial Sequence
<220> FEATURE:
<223> OTHER INFORMATION: A synthetic oligonucleotide -continued

<400> SEQUENCE: 8
caactcctcg agtcacttat cgtcgtcatc cttgtaatcg aacgtttctt tgttgaagta    60
gaatt    65

<210> SEQ ID NO 9
<211> LENGTH: 9
<212> TYPE: PRT
<213> ORGANISM: Artificial Sequence
<220> FEATURE:
<223> OTHER INFORMATION: A synthetic polypeptide

<400> SEQUENCE: 9

Lys Leu Lys Thr Gln Lys Ile Tyr Phe
 1               5

<210> SEQ ID NO 10
<211> LENGTH: 13
<212> TYPE: PRT
<213> ORGANISM: Artificial Sequence
<220> FEATURE:
<223> OTHER INFORMATION: A synthetic polypeptide

<400> SEQUENCE: 10

Leu Glu Pro Met Asp Phe Leu Gly Lys Ala Lys Val Val
 1               5                   10

<210> SEQ ID NO 11
<211> LENGTH: 11
<212> TYPE: PRT
<213> ORGANISM: Artificial Sequence
<220> FEATURE:
<223> OTHER INFORMATION: A synthetic polypeptide
<221> NAME/KEY: SITE
<222> LOCATION: 1, 11
<223> OTHER INFORMATION: Xaa = any amino acid or absent
<221> NAME/KEY: SITE
<222> LOCATION: 2, 4, 6, 7,
<223> OTHER INFORMATION: Xaa = K, N, Q or H
<221> NAME/KEY: SITE
<222> LOCATION: 3, 8
<223> OTHER INFORMATION: Xaa = L, I, A, G or V
<221> NAME/KEY: SITE
<222> LOCATION: 5
<223> OTHER INFORMATION: Xaa = T, S, D, E or Y

<400> SEQUENCE: 11

Xaa Xaa Xaa Xaa Xaa Xaa Xaa Xaa Tyr Phe Xaa
 1               5                   10

<210> SEQ ID NO 12
<211> LENGTH: 9
<212> TYPE: PRT
<213> ORGANISM: Artificial Sequence
<220> FEATURE:
<223> OTHER INFORMATION: A synthetic polypeptide
<221> NAME/KEY: SITE
<222> LOCATION: 1
<223> OTHER INFORMATION: Xaa = K or N
<221> NAME/KEY: SITE
<222> LOCATION: 5
<223> OTHER INFORMATION: Xaa = K or Q

<400> SEQUENCE: 12

Xaa Leu Lys Thr Xaa Lys Ile Tyr Phe
 1               5

<210> SEQ ID NO 13

```
<211> LENGTH: 11
<212> TYPE: PRT
<213> ORGANISM: Artificial Sequence
<220> FEATURE:
<223> OTHER INFORMATION: A synthetic polypeptide
<221> NAME/KEY: SITE
<222> LOCATION: 1, 11
<223> OTHER INFORMATION: Xaa = any amino acid or absent
<221> NAME/KEY: SITE
<222> LOCATION: 2, 6
<223> OTHER INFORMATION: Xaa = K, N, Q or H
<221> NAME/KEY: SITE
<222> LOCATION: 5
<223> OTHER INFORMATION: Xaa= T, S, D, E or Y
<221> NAME/KEY: SITE
<222> LOCATION: 8
<223> OTHER INFORMATION: Xaa = L, I, A, G or V

<400> SEQUENCE: 13

Xaa Xaa Leu Lys Xaa Xaa Lys Xaa Tyr Phe Xaa
  1               5                  10

<210> SEQ ID NO 14
<211> LENGTH: 11
<212> TYPE: PRT
<213> ORGANISM: Artificial Sequence
<220> FEATURE:
<223> OTHER INFORMATION: A synthetic polypeptide
<221> NAME/KEY: SITE
<222> LOCATION: 1, 11
<223> OTHER INFORMATION: Xaa = any amino acid or absent
<221> NAME/KEY: SITE
<222> LOCATION: 2, 6
<223> OTHER INFORMATION: Xaa = K, N, Q, or H
<221> NAME/KEY: SITE
<222> LOCATION: 3, 8
<223> OTHER INFORMATION: Xaa = L, A, I or V

<400> SEQUENCE: 14

Xaa Xaa Xaa Lys Thr Xaa Lys Xaa Tyr Phe Xaa
  1               5                  10

<210> SEQ ID NO 15
<211> LENGTH: 9
<212> TYPE: PRT
<213> ORGANISM: Artificial Sequence
<220> FEATURE:
<223> OTHER INFORMATION: A synthetic polypeptide

<400> SEQUENCE: 15

Arg Lys Lys Arg Arg Gln Arg Arg Arg
  1               5

<210> SEQ ID NO 16
<211> LENGTH: 9
<212> TYPE: PRT
<213> ORGANISM: Artificial Sequence
<220> FEATURE:
<223> OTHER INFORMATION: A synthetic polypeptide

<400> SEQUENCE: 16

Cys Gly Asn Lys Arg Thr Arg Gly Cys
  1               5

<210> SEQ ID NO 17
<211> LENGTH: 564
<212> TYPE: PRT
<213> ORGANISM: Mus musculus

<400> SEQUENCE: 17
```

```
Met Gly Asn Trp Leu Val Asn His Trp Leu Ser Val Leu Phe Leu Val
1               5                   10                  15

Ser Trp Leu Gly Leu Asn Ile Phe Leu Phe Val Tyr Ala Phe Leu Asn
            20                  25                  30

Tyr Lys Lys Ser Asp Lys Tyr Tyr Thr Arg Arg Ile Leu Gly Thr
        35                  40                  45

Ala Leu Ala Leu Ala Arg Ala Ser Ala Leu Cys Leu Asn Phe Asn Ser
50                  55                  60

Met Met Ile Leu Ile Pro Val Cys Arg Asn Leu Ser Phe Leu Arg
65                  70                  75                  80

Gly Thr Cys Ser Phe Cys Asn Arg Thr Leu Arg Lys Phe Leu Asp His
                85                  90                  95

Asn Leu Thr Phe His Lys Leu Val Ala Tyr Met Ile Cys Ile Phe Thr
        100                 105                 110

Val Ile His Ile Ile Ala His Leu Phe Asn Phe Glu Arg Tyr Arg Arg
        115                 120                 125

Ser Gln Gln Ala Asn Asp Gly Ser Leu Ala Ser Val Leu Ser Ser Leu
    130                 135                 140

Ser His Pro Lys Lys Glu Asp Ser Trp Leu Asn Pro Ile Gln Ser Pro
145                 150                 155                 160

Asn Met Thr Val Met Tyr Ala Ala Phe Thr Ser Ile Ala Gly Leu Thr
                165                 170                 175

Gly Val Ile Ala Thr Val Ala Leu Val Leu Met Val Thr Ser Ala Met
            180                 185                 190

Glu Phe Phe Ile Arg Arg Asn Tyr Phe Glu Leu Phe Trp Tyr Thr His
            195                 200                 205

His Leu Phe Ile Val Tyr Ile Ile Cys Leu Gly Ile His Gly Leu Gly
    210                 215                 220

Gly Ile Val Arg Gly Gln Thr Glu Glu Ser Leu Gly Glu Ser His Pro
225                 230                 235                 240

His Asn Cys Ser His Ser Phe His Glu Trp Asp Asp His Lys Gly Ser
                245                 250                 255

Cys Arg His Pro His Phe Ala Gly His Pro Pro Glu Ser Trp Lys Trp
                260                 265                 270

Ile Leu Ala Pro Ile Ala Phe Tyr Ile Phe Glu Arg Ile Leu Arg Phe
    275                 280                 285

Tyr Arg Ser Gln Gln Lys Val Val Ile Thr Lys Val Val Met His Pro
    290                 295                 300

Ser Asn Val Leu Glu Leu Gln Met Arg Lys Arg Gly Phe Ser Met Glu
305                 310                 315                 320

Val Gly Gln Tyr Ile Phe Val Asn Cys Pro Ser Ile Ser Phe Leu Glu
            325                 330                 335

Asn His Pro Phe Thr Leu Thr Ser Ala Pro Lys Glu Glu Phe Phe Ser
            340                 345                 350

Val His Ile Arg Ala Ala Gly Asp Asn Thr Arg Asn Leu Ile Arg Thr
        355                 360                 365

Phe Glu Gln Gln His Ser Pro Met Pro Arg Ile Glu Val Asp Gly Pro
370                 375                 380

Phe Gly Thr Val Ser Glu Asp Val Phe Gln Tyr Glu Val Ala Val Leu
385                 390                 395                 400

Val Gly Ala Gly Ile Gly Val Thr Pro Phe Ala Ser Ile Leu Lys Ser
                405                 410                 415

Ile Trp Tyr Lys Phe Gln Arg Ala Asp Asn Lys Leu Lys Thr Gln Lys
```

```
            420                 425                 430
Ile Tyr Phe Tyr Trp Ile Cys Arg Glu Thr Gly Ala Phe Ala Trp Phe
            435                 440                 445

Asn Asn Leu Leu Asn Ser Leu Glu Gln Glu Met Glu Glu Leu Gly Lys
        450                 455                 460

Met Asp Phe Leu Asn Tyr Arg Leu Phe Leu Thr Gly Trp Asp Ser Asn
465                 470                 475                 480

Ile Ala Gly His Ala Ala Leu Asn Phe Asp Arg Ala Thr Asp Ile Leu
                485                 490                 495

Thr Gly Leu Lys Gln Lys Thr Ser Phe Gly Arg Pro Met Trp Asp Asn
            500                 505                 510

Glu Phe Ser Arg Ile Ala Thr Ala His Pro Lys Ser Ala Val Gly Val
        515                 520                 525

Phe Leu Cys Gly Pro Arg Thr Leu Ala Lys Ser Leu Arg Lys Cys Cys
    530                 535                 540

His Arg Tyr Ser Ser Leu Asp Pro Arg Lys Val Gln Phe Tyr Phe Asn
545                 550                 555                 560

Lys Glu Thr Phe
```

<210> SEQ ID NO 18
<211> LENGTH: 564
<212> TYPE: PRT
<213> ORGANISM: Rattus norvegicus

<400> SEQUENCE: 18

```
Met Gly Asn Trp Leu Val Asn His Trp Leu Ser Val Leu Phe Leu Val
1               5                   10                  15

Ser Trp Leu Gly Leu Asn Ile Phe Leu Phe Val Tyr Ala Phe Leu Asn
            20                  25                  30

Tyr Lys Lys Ser Asp Lys Tyr Tyr Tyr Thr Arg Glu Ile Leu Gly Thr
        35                  40                  45

Ala Leu Ala Leu Ala Arg Ala Ser Ala Leu Cys Leu Asn Phe Lys Ser
    50                  55                  60

Met Val Ile Leu Ile Pro Val Cys Arg Asn Leu Leu Ser Phe Leu Arg
65                  70                  75                  80

Gly Thr Cys Ser Phe Cys Asn His Thr Leu Arg Lys Pro Leu Asp His
                85                  90                  95

Asn Leu Thr Phe His Lys Leu Val Ala Tyr Met Ile Cys Ile Phe Thr
            100                 105                 110

Ala Ile His Ile Ile Ala His Leu Phe Asn Phe Glu Arg Tyr Ser Arg
        115                 120                 125

Ser Gln Gln Ala Asn Asp Cys Ser Leu Ala Ser Val Leu Ser Ser Leu
    130                 135                 140

Phe His Pro Glu Lys Glu Asp Ser Trp Leu Asn Pro Ile Gln Ser Pro
145                 150                 155                 160

Asn Val Thr Val Met Tyr Ala Ala Phe Thr Ser Ile Ala Gly Leu Thr
                165                 170                 175

Gly Val Val Ala Thr Val Ala Leu Val Leu Met Val Thr Ser Ala Met
            180                 185                 190

Glu Phe Ile Arg Arg Asn Tyr Phe Glu Leu Phe Trp Tyr Thr His His
        195                 200                 205

Leu Phe Ile Ile Tyr Ile Ile Cys Leu Cys His Gly Leu Gly Gly
    210                 215                 220

Ile Val Arg Gly Gln Thr Glu Arg Ser Asn Ser Arg Ser His Pro Arg
```

```
                225                 230                 235                 240
Asn Cys Ser Tyr Ser Phe His Glu Trp Asp Lys Tyr Glu Arg Ser Cys
                    245                 250                 255

Arg Ser Pro His Phe Val Cys Gln Asp Pro Glu Ser Trp Lys Trp
                260                 265                 270

Ile Leu Ala Pro Ile Ala Phe Tyr Ile Phe Glu Arg Ile Leu Arg Phe
                275                 280                 285

Tyr Arg Ser Arg Gln Lys Val Val Ile Thr Lys Val Val Met His Pro
                290                 295                 300

Cys Lys Val Leu Glu Leu Gln Met Arg Lys Arg Gly Phe Thr Met Gly
305                 310                 315                 320

Ile Gly Gln Tyr Ile Phe Val Asn Cys Pro Ser Ile Ser Phe Leu Glu
                    325                 330                 335

Trp His Pro Phe Thr Leu Thr Ser Ala Pro Glu Glu Glu Phe Phe Ser
                340                 345                 350

Ile His Ile Arg Ala Ala Gly Asp Trp Thr Glu Asn Leu Ile Arg Thr
                355                 360                 365

Phe Glu Gln Gln Glu Ser Pro Met Pro Arg Ile Glu Val Asp Gly Pro
370                 375                 380

Phe Gly Thr Val Ser Glu Asp Val Phe Gln Tyr Glu Val Ala Val Leu
385                 390                 395                 400

Val Gly Ala Gly Ile Gly Tyr Thr Pro Phe Ala Ser Phe Leu Lys Ser
                    405                 410                 415

Ile Trp Tyr Lys Phe Gln Arg Ala His Asn Lys Leu Lys Thr Gln Lys
                420                 425                 430

Ile Tyr Phe Tyr Trp Ile Cys Arg Glu Thr Gly Ala Phe Ala Trp Phe
                435                 440                 445

Asn Asn Leu Leu Asn Ser Leu Glu Gln Glu Met Asp Glu Leu Gly Lys
                450                 455                 460

Asp Asp Phe Leu Asn Tyr Arg Leu Phe Leu Thr Gly Trp Asp Ser Asn
465                 470                 475                 480

Ile Ala Gly His Ala Ala Leu Asn Phe Asp Arg Ala Thr Asp Val Leu
                    485                 490                 495

Thr Gly Leu Lys Gln Lys Thr Ser Phe Gly Arg Pro Met Trp Asp Asn
                500                 505                 510

Glu Phe Ser Arg Ile Ala Thr Ala His Pro Lys Ser Val Val Gly Val
                515                 520                 525

Phe Leu Cys Gly Pro Arg Thr Leu Ala Lys Ser Leu Arg Lys Cys Cys
530                 535                 540

Arg Arg Tyr Ser Ser Leu Asp Pro Arg Lys Val Gln Phe Tyr Phe Asn
545                 550                 555                 560

Lys Glu Thr Phe

<210> SEQ ID NO 19
<211> LENGTH: 564
<212> TYPE: PRT
<213> ORGANISM: Homo sapiens

<400> SEQUENCE: 19

Met Gly Asn Trp Val Val Asn His Trp Phe Ser Val Leu Phe Leu Val
1               5                   10                  15

Val Trp Leu Gly Leu Asn Val Phe Leu Phe Val Asp Ala Phe Leu Lys
                20                  25                  30

Tyr Glu Lys Ala Asp Lys Tyr Tyr Tyr Thr Arg Lys Ile Leu Gly Ser
```

```
                35                  40                  45
Thr Leu Ala Cys Ala Arg Ala Ser Ala Leu Cys Leu Asn Phe Lys Ser
 50                  55                  60

Thr Leu Ile Leu Leu Pro Val Cys Arg Asn Leu Leu Ser Phe Leu Arg
 65                  70                  75                  80

Gly Thr Cys Ser Phe Cys Ser Arg Thr Leu Arg Lys Gln Leu Asp His
                 85                  90                  95

Asn Leu Thr Phe His Lys Leu Val Ala Tyr Asn Ile Cys Leu His Thr
            100                 105                 110

Ala Ile His Ile Ile Ala His Leu Phe Asn Phe Asp Cys Tyr Ser Arg
        115                 120                 125

Ser Arg Gln Ala Thr Asp Gly Ser Leu Ala Ser Ile Leu Ser Ser Leu
    130                 135                 140

Ser His Asp Glu Lys Lys Gly Gly Ser Trp Leu Asn Pro Ile Gln Ser
145                 150                 155                 160

Ser Asn Thr Ile Val Glu Tyr Val Thr Phe Thr Ser Ile Ala Gly Leu
                165                 170                 175

Thr Gly Val Ile Met Thr Ile Ala Leu Ile Leu Asn Val Thr Ser Ala
            180                 185                 190

Thr Glu Phe Ile Arg Arg Ser Tyr Phe Lys Val Phe Trp Tyr Thr Asn
        195                 200                 205

His Leu Phe Ile Phe Tyr Ile Leu Gly Ile Gly Ile His Gly Ile Gly
    210                 215                 220

Gly Ile Val Arg Gly Gln Thr Lys Lys Ser Asn Asn Lys Ser His Pro
225                 230                 235                 240

Pro Lys Cys Ala Glu Ser Phe Glu Asn Trp Asp Asp Arg Asp Ser His
                245                 250                 255

Cys Arg Arg Pro Lys Phe Lys Gly His Pro Phe Lys Ser Trp Lys Trp
            260                 265                 270

Ile Leu Ala Pro Val Ile Leu Tyr Ile Cys Lys Arg Ile Leu Arg Phe
        275                 280                 285

Tyr Arg Ser Gln Gln Lys Val Val Ile Thr Lys Val Val Met His Pro
    290                 295                 300

Ser Lys Val Leu Glu Leu Gln Met Asn Lys Arg Gly Phe Ser Met Glu
305                 310                 315                 320

Val Gly Gln Tyr Ile Phe Val Asn Cys Pro Ser Ile Ser Leu Leu Glu
                325                 330                 335

Trp His Pro Phe Thr Leu Thr Ser Ala Pro Glu Glu Asp Phe Phe Ser
            340                 345                 350

Ile His Ile Arg Ala Ala Gly Asp Trp Thr Glu Asn Leu Ile Arg Ala
        355                 360                 365

Phe Glu Gln Gln Tyr Ser Pro Ile Pro Arg Ile Glu Val Asp Gly Pro
    370                 375                 380

Phe Gly Thr Ala Ser Glu Asp Val Phe Gln Tyr Glu Val Ala Val Leu
385                 390                 395                 400

Val Gly Ala Gly Ile Gly Val Thr Pro Phe Ala Ser Ile Leu Lys Ser
                405                 410                 415

Ile Trp Tyr Lys Phe Gln Cys Ala Asp His Asn Leu Lys Thr Lys Lys
            420                 425                 430

Ile Tyr Phe Tyr Trp Ile Cys Arg Glu Thr Gly Ala Phe Ser Asn Phe
        435                 440                 445

Asn Asn Leu Leu Thr Ser Leu Glu Gln Glu Met Glu Glu Leu Gly Lys
    450                 455                 460
```

```
Val Gly Phe Leu Asn Tyr Arg Leu Phe Leu Thr Gly Trp Asp Ser Asn
465                 470                 475                 480

Ile Val Gly His Ala Ala Leu Asn Phe Asp Lys Ala Thr Asp Ile Val
                485                 490                 495

Thr Gly Leu Lys Gln Lys Thr Ser Phe Gly Arg Pro Met Trp Asp Asn
            500                 505                 510

Glu Phe Ser Thr Leu Ala Thr Ser His Pro Lys Ser Val Val Gly Val
            515                 520                 525

Phe Leu Cys Gly Pro Arg Thr Leu Ala Lys Ser Leu Arg Lys Cys Cys
            530                 535                 540

His Arg Tyr Ser Ser Leu Asp Pro Arg Lys Val Gln Phe Tyr Phe Asn
545                 550                 555                 560

Lys Glu Asn Phe

<210> SEQ ID NO 20
<211> LENGTH: 9
<212> TYPE: PRT
<213> ORGANISM: Artificial Sequence
<220> FEATURE:
<223> OTHER INFORMATION: A synthetic polypeptide

<400> SEQUENCE: 20

Lys Leu Lys Thr Gln Lys Ile Tyr Phe
1               5

<210> SEQ ID NO 21
<211> LENGTH: 5
<212> TYPE: PRT
<213> ORGANISM: Artificial Sequence
<220> FEATURE:
<223> OTHER INFORMATION: A synthetic polypeptide

<400> SEQUENCE: 21

Gln Lys Ile Tyr Phe
1               5
```

PEPTIDE INHIBITOR OF NOX1 NADPH OXIDASE

CROSS-REFERENCE TO RELATED APPLICATIONS

This application claims the benefit of the filing date of U.S. application Ser. No. 62/013,916, filed on Jun. 18, 2014, the disclosure of which is incorporated by reference herein.

GOVERNMENT GRANT SUPPORT

This invention was made with U.S. Government support under HL081750 awarded by the National Institutes of Health and under 1BX001729 awarded by The Department of Veterans Affairs. The Government has certain rights in the invention.

BACKGROUND

Nox1 serves as the catalytic core of a multi-subunit NADPH oxidase enzyme complex, which assembles in response to signaling cascades initiated by mechanical stress, cytokines and growth factors. Nox1 is a transmembrane protein expressed in multiple tissues including vascular smooth muscle cells (VSMCs), brain, gastrointestinal epithelium, and prostate tumor cells (Fukui et al., 1995; Reinehr et al., 2007; Rokutan et al., 2006; Lim et al., 2005). Nox1 plays a critical role in the development of cardiovascular disease (CVD), amyotropic lateral sclerosis (ALS), gastrointestinal disease, immunological disorders, and multiple forms of cancer (Leto and Geiszt, 2005; Lambeth, 2004; Sumimoto et al., 1994).

Since its discovery in 1999, multiple studies have provided evidence that activation of Nox1 is a multi-step process that requires assembly of a complex of proteins (Lassegue et al., 2012). Nox1 associates with the transmembrane protein p22$^{phox}$ for stability and membrane localization. The recruitment of cytosolic proteins to the membrane forms a complex which allows electron transfer from NADPH to oxygen to form superoxide (Hanna et al., 2004; Banfi et al., 2003; Lambeth, 2004). When activated, the organizer cytosolic protein p47$^{phox}$ or its homolog NoxO1 tethers to p22$^{phox}$ (Huang et al., 1999; Debbabi et al., 2013; Kawahara et al., 2005). Recruitment of the activator p67$^{phox}$ or its homolog NoxA1 is mediated via tail-to-tail binding to the organizer protein (Huang et al., 1999; Debbabi et al., 2013; Kawahara et al., 2005). Mutation of the "activation domain" of NoxA1 abrogates Nox1-generated ROS (Maehara et al., 2010). However, the molecular interaction of Nox1 with the activation domain of NoxA1 is not known. Phosphorylation of NoxA1 allows for dissociation from Nox1 and is one mechanism to terminate enzyme activity (Kobayashi et al., 1989). Whether post-translational modifications of Nox1 regulate its activation has not been explored.

SUMMARY OF THE INVENTION

The invention provides an isolated peptide and a fusion protein having the peptide, and nucleic acid vectors comprising nucleic acid sequences comprising an open reading frame encoding the peptide or fusion protein, useful to interfere with the phosphorylation of Nox1, block or inhibit binding of NoxA1 activation domain (AD) to Nox1, and/or prevent or inhibit assembly of the p47phox/NoxA1 complex with Nox1. In one embodiment, the fusion protein optionally includes a targeting peptide, e.g., one useful to transport linked molecules across a cell membrane and/or a nuclear membrane or target a specific cell for instance via a cell surface receptor, a protease cleavage site, a peptide useful to isolate the fusion protein from a mixture, or any combination thereof. In one embodiment, the fusion protein optionally includes a targeting molecule that is not a peptide.

NADPH oxidases are multi-subunit cellular enzymes whose primary function is to generate oxygen free radicals. These free radicals are important in many normal cellular functions (e.g. immune function and cell signaling), as well as contribute to the development of many diseases (e.g. cardiovascular disease and cancers). The catalytic subunit of the complex is the Nox subunit. There are multiple homologs of the Nox subunit, and their expression and function dependent on the particular cell and tissue type. Nox1 is primarily expressed in vascular cells and the colon. In vascular cells, activation of Nox1 contributes to pathogenesis of hypertension, atherosclerosis, restenosis, endothelial dysfunction, and bypass graft failure. As described herein, a short peptide was identified that interferes with the phosphorylation of Nox1 and prevents assembly of the p47phox/NoxA1 complex with Nox1. In particular, the data reveal that PKC-β1 phosphorylation of Nox1 at T429 is necessary for its interaction with NoxA1 activation domain, complex assembly, and generation of superoxide, and that peptides within the scope of this disclosure may be phosphorylated in vivo by PKC. In addition, the peptide inhibits smooth muscle cell (SMC) migration induced by multiple agonists and inhibits the cellular production of reactive oxygen species (ROS). Furthermore, mutation of T429 prevents Nox1-mediated vascular smooth muscle cell (VSMC) migration. These findings identify a novel regulatory mechanism by which Nox1 is activated. The mechanism by which the peptide interferes with Nox1 activation likely involves competitive inhibition with the NoxA1 activation domain and/or inhibition of protein kinase C-mediated phosphorylation of Nox1. The net effect is that the peptide "turns off" Nox1, resulting in decreased ROS production and abrogation of ensuing pathogenic phenotypes. The prevention of the activation of Nox1 has broad implications for the treatment of a variety of cardiovascular diseases, inflammatory diseases, neurodegenerative diseases, and cancers that rely on Nox1, and other diseases for which Nox1 activation is a key driving factor. Therefore, the peptide of the invention is useful to inhibit or block, e.g. selectively inhibit or block, Nox1 activity in a variety of disease settings. Further, because the peptide is selective, it is likely to be a more efficient inhibitor than RNA inhibitors, e.g., Nox1 siRNA, and chemical inhibitors such as apocynin.

Thus, the invention provides isolated peptides and fusion proteins comprising the peptide(s). In one embodiment, the fusion protein includes a peptide sequence suitable for purification or isolation, e.g., a his-tag, a glutathione S-transferase (GST) peptide sequence, maltose binding protein (MBP) peptide sequence or a chitin binding peptide sequence, a cell targeting peptide or nucleic acid (e.g., aptamer), a membrane transport peptide, and/or a protease cleavage site, e.g., thrombin cleavage site, enterokinase cleavage site, tobacco etch virus (TEV) protease cleavage site, factor Xa cleavage site, or a HRV3C protease cleavage site. In one embodiment, RNA aptamers with cell targeting activity are fused to a peptide of the invention. For example, prostate specific membrane antigen (PSMA) binding RNA aptamers (see, e.g., FIG. 1 in Dassie et al., 2009, and FIGS. 1B and 2A in Rocky et al., 2011), HER2 binding RNA aptamers (see FIG. 1 in Thiel et al., 2010 and hHER2-apt in Kim et al., 2011), and VSMC binding RNA aptamers (see, e.g., Figure S5 in Thiel et al., 2012), the disclosures of which are incorporated by reference herein, may be fused to a peptide of the invention.

In one embodiment, the invention provides an isolated peptide or fusion protein comprising the peptide, wherein the peptide has formula (I): $Z_1-X_1-X_2-X_1-X_3-X_1-X_1-X_2-Y-F-Z_1$ (SEQ ID NO: 1), wherein each $X_1$ is independently K, N, Q, or H; wherein each $X_2$ is independently L, I, A, G or V; wherein $X_3$ is T, S, D, E, or Y; and wherein each $Z_1$ is independently absent, or is 1 to 50 amino acids in length. In one embodiment, $X_3$ is T. In one embodiment, $X_3$ is D or E. In one embodiment, the peptide comprises K/N-L-K-T-K/Q-K-I-Y-F (SEQ ID NO:12). In one embodiment, the peptide comprises $Z_1-X_1-L-K-X_3-X_1-K-X_2-Y-F-Z_1$ (SEQ ID NO:13), wherein each $X_1$ is independently K, N, Q, or H; wherein $X_2$ is independently L, I, A, G or V; and wherein each $Z_1$ is independently absent, or is 1 to 50 amino acids in length. In one embodiment, the peptide comprises $Z_1-X_1-X_2-K-T-X_1-K-X_2-Y-F-Z_1$ (SEQ ID NO:14), wherein each $X_1$ is independently K, N, Q, or H; wherein each $X_2$ is independently L, A, I, or V; wherein $X_3$ is T, S or Y; and wherein each $Z_1$ is independently absent; or is 1 to 50 amino acids in length. In one embodiment, the isolated peptide or fusion protein is no more than 100 amino acids in length. In one embodiment; the isolated peptide or fusion protein is no more than 50 amino acids in length. In one embodiment, the isolated peptide or fusion protein is no more than 20 amino acids in length. In one embodiment, the isolated peptide or fusion protein is no more than 10 amino acids in length. In one embodiment, the fusion protein comprises a targeting peptide, e.g., cell membrane and/or nuclear membrane transport including but not limited to RrRK (lower case indicates D conformation), RKKRRQRRR (SEQ ID NO:23), CGNKRTRGC (SEQ ID NO:24), Oct4PTD, or penetratin, a cell type specific peptide, e.g., that binds to a cell surface receptor, or a non-peptide targeting molecule, such as a nucleic acid aptamer.

In one embodiment, the peptide is at least 5 to about 30 amino acids in length that include a contiguous sequence of SEQ ID NO:11, e.g., from about 9 to about 20 amino acids in length or about 10 to about 30 amino acids (or any integer in between 5 and 30) in length, such as 10 to 15 amino acids in length. In one embodiment, the isolated peptide or fusion protein is no more than 1000 amino acids in length. In another embodiment, the isolated peptide or fusion protein is no more than 500 amino acids in length. In a further embodiment, the isolated peptide or fusion protein is no more than 100 amino acids in length. In yet another embodiment, the isolated peptide or fusion protein is no more than 50 amino acids in length. A fused protein may have a peptide domains that may replace one or more domains or sequences in a larger polypeptide sequence, for instance, a naturally occurring polypeptide, or may be inserted into or at one or both ends, or any combination thereof, of a larger polypeptide sequence, e.g., a naturally occurring polypeptide.

In one embodiment, an isolated peptide or a fusion protein has a sequence that includes at least 3, 4, 5, 6, 7, 8 or 9 of the residues in SEQ ID NO:9, which peptide or fusion protein interferes with the phosphorylation of Nox1, blocks or inhibits binding of NoxA1 activation domain (AD) to Nox1, and/or prevents or inhibits assembly of the p47phox/NoxA1 complex with Nox1. In one embodiment, the isolated peptide or a fusion protein has a sequence that includes at least 3, 4, 5, 6, 7, 8 or 9 contiguous residues in SEQ ID NO:9, 12, 13, or 14.

Also described herein are recombinant nucleic acids (expression cassettes) encoding a peptide or a fusion protein. In one embodiment, the peptide may be expressed as an artificial recombinant fusion protein. In one embodiment, the peptide or fusion protein is expressed in an insect or mammalian cell. Bacterial strains can be engineered to overexpress the peptide or fusion protein in a manner that makes it easy to separate from the bacterial culture or extract of the bacteria. For example, the fusions are either genetically engineered for secretion into the media, or engineered to coalesce into bacterial protein bodies, e.g., inclusion bodies. In another embodiment, the fusion protein may include additional peptide domains that impart easy separation (isolation) from mixtures. Examples of such domains are binding domain that imparts a second partner target binding ability so that the fusion protein can be isolated by binding to a substrate containing the second binding partner.

Further provided is a pharmaceutical composition comprising an isolated peptide or fusion protein comprising the peptide, wherein the peptide has formula (I):

$$Z_1-X_1-X_2-X_1-X_3-X_1-X_1-X_2-Y-F-Z_1 \quad \text{(SEQ ID NO: 11)}$$

wherein each $X_1$ is independently K, N, Q, or H; wherein each $X_2$ is independently L, I, A, G or V; wherein $X_3$ is T, S, D, E, or Y; and wherein each $Z_1$ is independently absent, or is 1 to 50 amino acids in length. In one embodiment, $X_3$ is T. In one embodiment, $X_3$ is D or E. In one embodiment, the isolated peptide or fusion protein is no more than 100 amino acids in length. In one embodiment, the isolated peptide or fusion protein is no more than 50 amino acids in length. In one embodiment, the isolated peptide or fusion protein is no more than 20 amino acids in length. In one embodiment, the isolated peptide or fusion protein is no more than 10 amino acids in length. In one embodiment, the fusion protein comprises a targeting peptide, e.g., cell membrane and/or nuclear membrane transport including but not limited to RrRK (lower case indicates D conformation), RKKRRQRRR (SEQ ID NO:23), CGNKRTRGC (SEQ ID NO:24), Oct4PTD, or penetratin, a cell type specific peptide, e.g., that binds to a cell surface receptor, or a non-peptide targeting molecule, such as a nucleic acid aptamer. A peptide or fusion protein may be delivered in any delivery vehicle, e.g., a liposome, or a microparticle or a nanoparticle, such as one formed of a biocompatible and/or biodegradable material, e.g., extracellular matrix or chitosan. In one embodiment, a peptide or fusion protein of the invention is combined with a non-ionic polymer, non-ionic copolymer, or monomers for a non-ionic copolymer, e.g., Pluronic gel.

Further provided is a recombinant nucleic acid vector comprising a nucleotide sequence encoding the peptide or fusion protein. In one embodiment, the nucleotide sequence is part of a recombinant viral genome in a recombinant virus.

The invention also provides a method to prevent, inhibit or treat a mammal having or at risk of a disorder or disease associated with Nox1 activation. The method includes administering to a mammal, e.g., a mouse, rat, rabbit, ferret, swine, equine, ovine, bovine, canine, feline, non-human primater, or a human, an effective amount of the peptide or fusion protein, or nucleic acid vector, of the invention. In one embodiment, the disorder or disease is hypertension, atherosclerosis, restenosis, bypass graft failure, or endothelial dysfunction. In one embodiment, the disorder or disease is cancer, e.g., prostate, melanoma, breast or colon cancer. In one embodiment, the disorder or disease is an inflammatory disease such as inflammatory bowel syndrome, e.g., ulcerative colitis or Crohn's disease, Parkinson's disease or diabetic retinopathy.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 8. Identification of putative Nox1 phosphorylation sites by NetPhosK. Method: NetPhosK without ESS (Evolutionary Stable Sites) filtering. Input: Rat Nox1 sequence. Score: Output score in the range of 0.000-1.000. A higher score indicates a higher confidence of prediction. Highlighted residues (T429 and T89) were examined. Abbreviations: T: threonine, S: serine, PKB: Protein Kinase B, PKC: Protein Kinase C, PKA: Protein Kinase A, DNAPK: DNA-dependent Protein Kinase, CKI: Casein Kinase I, P38MAPK: p38 Mitogen-Activated Kinase, CKII: Casein Kinase II, CDC2: Cell Division Cycle Protein 2, PKG: cGMP-dependent Protein Kinase, INSR: Insulin Receptor, RSK: Ribosomal s6 Kinase, CDK5: Cell Division Protein Kinase 5.

FIG. 10. Sequence alignment of mouse, rat and human Nox1 (SEQ ID Nos. 17-19). Nox1 transmembrane domains (TM) are indicated in light gray, denoted as I-VI. Intracellular loops are indicated in green. Extracellular domains are indicated in blue. The C-terminal domain is not shaded. Predicted phosphorylation sites that were analyzed in this study are indicated in red and are conserved across mouse, rat and human Nox1.

DETAILED DESCRIPTION

Definitions

Figure 1:
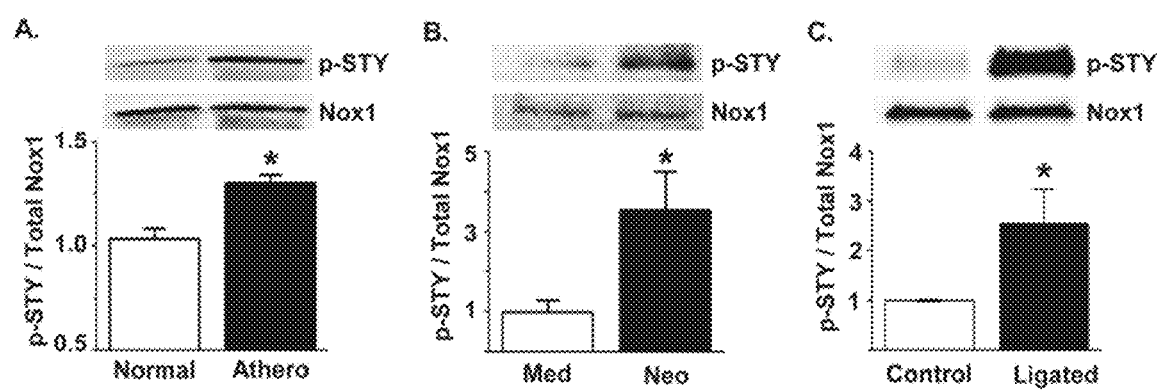
FIG. 1. Nox1 phosphorylation is increased in multiple models of vascular disease. Nox1 phosphorylation was assessed by subjecting lysates to immunoprecipitation with anti-p22$^{phox}$ followed by Western blotting with either anti-STY or anti-Nox1. (A) Aorta from monkeys fed a normal or atherogenic (Athero) diet. (B) Cultured medial (Med) and neointimal (Neo) VSMCs derived from rat aorta 14 days following balloon injury. (C) Murine carotid artery 3 days post-ligation. n=3-5 per group. *$p<0.05$ as compared to non-diseased.

A "vector" refers to a macromolecule or association of macromolecules that comprises or associates with a polynucleotide, and which can be used to mediate delivery of the polynucleotide to a cell, either in vitro or in vivo. Illustrative vectors include, for example, plasmids, viral vectors, liposomes and other gene delivery vehicles. The polynucleotide to be delivered, sometimes referred to as a "target polynucleotide" or "transgene," may comprise a coding sequence of interest in gene therapy (such as a gene encoding a protein of therapeutic interest), a coding sequence of interest in vaccine development (such as a polynucleotide expressing a protein, polypeptide or peptide suitable for eliciting an immune response in a mammal), and/or a selectable or detectable marker.

"Transduction," "transfection," "transformation" or "transducing" as used herein, are terms referring to a process for the introduction of an exogenous polynucleotide into a host cell leading to expression of the polynucleotide, e.g., the transgene in the cell, and includes the use of recombinant virus to introduce the exogenous polynucleotide to the host cell. Transduction, transfection or transformation of a polynucleotide in a cell may be determined by methods well known to the art including, but not limited to, protein expression (including steady state levels), e.g., by ELISA, flow cytometry and Western blot, measurement of DNA and RNA by heterologousization assays, e.g., Northern blots, Southern blots and gel shift mobility assays. Methods used for the introduction of the exogenous polynucleotide include well-known techniques such as viral infection or transfection, lipofection, transformation and electroporation, as well as other non-viral gene delivery techniques. The introduced polynucleotide may be stably or transiently maintained in the host cell.

"Gene delivery" refers to the introduction of an exogenous polynucleotide into a cell for gene transfer, and may encompass targeting, binding, uptake, transport, localization, replicon integration and expression.

"Gene transfer" refers to the introduction of an exogenous polynucleotide into a cell which may encompass targeting, binding, uptake, transport, localization and replicon integration, but is distinct from and does not imply subsequent expression of the gene.

"Gene expression" or "expression" refers to the process of gene transcription, translation, and post-translational modification.

An "infectious" virus or viral particle is one that comprises a polynucleotide component which it is capable of delivering into a cell for which the viral species is trophic. The term does not necessarily imply any replication capacity of the virus.

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A "transcriptional regulatory sequence" refers to a genomic region that controls the transcription of a gene or coding sequence to which it is operably linked. Transcriptional regulatory sequences of use in the present invention generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

"Heterologous" means derived from a genotypically distinct entity from the entity to which it is compared. For example, a polynucleotide introduced by genetic engineering techniques into a different cell type is a heterologous polynucleotide (and, when expressed, can encode a heterologous polypeptide). Similarly, a transcriptional regulatory element such as a promoter that is removed from its native coding sequence and operably linked to a different coding sequence is a heterologous transcriptional regulatory element.

A "terminator" refers to a polynucleotide sequence that tends to diminish or prevent read-through transcription (i.e., it diminishes or prevent transcription originating on one side of the terminator from continuing through to the other side of the terminator). The degree to which transcription is disrupted is typically a function of the base sequence and/or the length of the terminator sequence. In particular, as is well known in numerous molecular biological systems, particular DNA sequences, generally referred to as "transcriptional termination sequences" are specific sequences that tend to disrupt read-through transcription by RNA polymerase, presumably by causing the RNA polymerase molecule to stop and/or disengage from the DNA being transcribed. Typical example of such sequence-specific terminators include polyadenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("uni-directional" terminators) or from both directions ("bi-directional" terminators), and may be comprised of sequence-specific termination sequences or sequence-non-specific terminators or both. A variety of such terminator sequences are known in the art; and illustrative uses of such sequences within the context of the present invention are provided below.

"Host cells," "cell lines," "cell cultures," "packaging cell line" and other such terms denote higher eukaryotic cells, such as mammalian cells including human cells, useful in the present invention, e.g., to produce recombinant virus or recombinant fusion polypeptide. These cells include the progeny of the original cell that was transduced. It is understood that the progeny of a single cell may not necessarily be completely identical (in morphology or in genomic complement) to the original parent cell.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters include AAV promoters, e.g., P5, P19, P40 and AAV ITR promoters, as well as heterologous promoters.

An "expression vector" is a vector comprising a region which encodes a gene product of interest, and is used for effecting the expression of the gene product in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

The terms "polypeptide" and "protein" are used interchangeably herein to refer to polymers of amino acids of any length. The terms also encompass an amino acid polymer that has been modified; for example, disulfide bond formation, glycosylation, acetylation, phosphonylation, lipidation, or conjugation with a labeling component.

An "isolated" polynucleotide, e.g., plasmid, virus, polypeptide or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Isolated nucleic acid, peptide or polypeptide is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded). Enrichment can be measured on an absolute basis, such as weight per volume of solution, or it can be measured in relation to a second, potentially interfering substance present in the source mixture. Increasing enrichments of the embodiments of this invention are increasingly preferred. Thus, for example, a 2-fold enrichment, 10-fold enrichment, 100-fold enrichment, or a 1000-fold enrichment.

The term "exogenous," when used in relation to a protein, gene, nucleic acid, or polynucleotide in a cell or organism refers to a protein, gene, nucleic acid, or polynucleotide which has been introduced into the cell or organism by artificial or natural means. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature, e.g., an expression cassette which links a promoter from one gene to an open reading frame for a gene product from a different gene.

"Transformed" or "transgenic" is used herein to include any host cell or cell line, which has been altered or augmented by the presence of at least one recombinant DNA sequence. The host cells of the present invention are typically produced by transfection with a DNA sequence in a plasmid expression vector, as an isolated linear DNA sequence, or infection with a recombinant viral vector.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of a selected sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); not less than 9 matches out of 10 possible base pair matches (90%), or not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. The two sequences or parts thereof are more homologous if their amino acids are greater than or equal to 50% identical when optimally aligned using the ALIGN program.

The term "corresponds to" is used herein to mean that a polynucleotide sequence is structurally related to all or a portion of a reference polynucleotide sequence, or that a polypeptide sequence is structurally related to all or a portion of a reference polypeptide sequence, e.g., they have at least 80%, 85%, 90%, 95% or more, e.g., 99% or 100%, sequence identity. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison.

As used herein, "substantially pure" or "purified" means an object species is the predominant species present (i.e., on a molar basis it is more abundant than any other individual species in the composition), for instance, a substantially purified fraction is a composition wherein the object species comprises at least about 50 percent (on a molar basis) of all macromolecular species present. Generally, a substantially pure composition will comprise more than about 80 percent of all macromolecular species present in the composition, or more than about 85%, about 90%, about 95%, and about 99%. The object species may be purified to essential homogeneity (contaminant species cannot be detected in the composition by conventional detection methods) wherein the composition consists essentially of a single macromolecular species.

NADPH Oxidase

NADPH oxidase (nicotinamide adenine dinucleotide phosphate-oxidase) is a membrane-bound enzyme complex. NADPH oxidase generates superoxide by transferring electrons from NADPH across the membrane and coupling these to molecular oxygen to produce superoxide anion, a reactive free-radical. Superoxide can be produced in intracellular vesicles and organelles, or it can be produced outside of the cell. Superoxide can either spontaneously or as catalyzed by superoxide dismutases, form hydrogen peroxide that can react with biomolecules or undergo further redox chemistry reactions.

NADPH oxidases are a major cause of vascular disease including atherosclerosis and restenosis, and NADPH oxidase inhibitors prevent progression if these diseases. Atherosclerosis is caused by the accumulation of macrophages containing cholesterol (foam cells) in artery walls (in the intima). NADPH oxidases produce reactive oxygen species (ROS). These ROS activate an enzyme that makes the macrophages adhere to the artery wall (by polymerizing actin fibers). This process is counterbalanced by NADPH oxidase inhibitors, and by antioxidants. An imbalance in favor of ROS produces atherosclerosis.

Exemplary Vascular Diseases

Examples of vascular conditions or vascular diseases to which the compositions and methods of the invention apply include atherosclerosis, preeclampsia, peripheral vascular disease, erectile dysfunction, cancers, renal failure, heart disease, stroke, maternal hypoxia (e.g., placental hypoxia, preeclampsia), abnormal pregnancy, peripheral vascular disease (e.g., arteriosclerosis), transplant accelerated arteriosclerosis, deep vein thrombosis, erectile dysfunction, cancers, renal failure, stroke, heart disease, sleep apnea, hypoxia during sleep, female sexual dysfunction, fetal hypoxia, smoking, anemia, hypovolemia, vascular or circulatory conditions which increase risk of metastasis or tumor progression, hemorrhage, hypertension, diabetes, vasculopathologies, surgery (e.g., per-surgical hypoxia, post-operative hypoxia), Raynaud's disease, endothelial dysfunction, regional perfusion deficits (e.g., limb, gut, renal ischemia), myocardial infarction, stroke, thrombosis, frost bite, decubitus ulcers, asphyxiation, poisoning (e.g., carbon monoxide, heavy metal), altitude sickness, pulmonary hypertension, sudden infant death syndrome (SIDS), asthma, chronic obstructive pulmonary disease (COPD), congenital circulatory abnormalities (e.g., Tetralogy of Fallot) and Erythroblastosis (blue baby syndrome). In one embodiment, the compositions of the invention are employed to prevent, inhibit or treat stroke, atherosclerosis, acute coronary syndromes including unstable angina, thrombosis and myocardial infarction, plaque rupture, both primary and secondary (in-stent) restenosis in coronary or peripheral arteries, transplantation-induced sclerosis, peripheral limb disease, intermittent claudication and diabetic complications (including ischemic heart disease, peripheral artery disease, congestive heart failure, retinopathy, neuropathy and nephropathy), or thrombosis.

Exemplary Cancers

Exemplary cancers to which the compositions and methods of the invention apply include a solid tumor located, e.g., in the ovary, breast, lung, thyroid, lymph node, kidney, ureter, bladder, ovary, teste, prostate, skin, bone, skeletal muscle, bone marrow, stomach, esophagus, small bowel, colon, rectum, pancreas, liver, smooth muscle, brain, e.g., malignant gliomas, spinal cord, nerves, ear, eye, nasopharynx, oropharynx, salivary gland, or the heart. For example, the compositions of the invention are useful to inhibit or treat prostate cancer, ovarian cancer, colon cancer, breast cancer, melanoma, leukemia, such as, for example, lymphomas, neuroblastoma, lung cancer, and the like, or other proliferative diseases. Additionally, the compositions of the present invention can be administered locally or systemically, alone or in combination with one or more anti-cancer agents.

Preparation of Expression Cassettes

To prepare expression cassettes encoding GTPase, for instance, Rac, SOD, a peptide thereof, or a fusion thereof, for transformation, the recombinant DNA sequence or segment may be circular or linear, double-stranded or single-stranded. A DNA sequence which encodes an RNA sequence that is substantially complementary to a mRNA sequence encoding a gene product of interest is typically a "sense" DNA sequence cloned into a cassette in the opposite orientation (i.e., 3' to 5' rather than 5' to 3'). Generally, the DNA sequence or segment is in the form of chimeric DNA, such as plasmid DNA, that can also contain coding regions flanked by control sequences which promote the expression of the DNA in a cell. As used herein, "chimeric" means that a vector comprises DNA from at least two different species, or comprises DNA from the same species, which is linked or associated in a manner which does not occur in the "native" or wild-type of the species.

Aside from DNA sequences that serve as transcription units, or portions thereof, a portion of the DNA may be untranscribed, serving a regulatory or a structural function. For example, the DNA may itself comprise a promoter that is active in eukaryotic cells, e.g., mammalian cells, or in certain cell types, or may utilize a promoter already present in the genome that is the transformation target of the lymphotrophic virus. Such promoters include the CMV promoter, as well as the SV40 late promoter and retroviral LTRs (long terminal repeat elements), although many other promoter elements well known to the art may be employed, e.g., the MMTV, RSV, MLV or HIV LTR in the practice of the invention.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The recombinant DNA to be introduced into the cells may contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, puro, hyg, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Exemplary reporter genes include the chloramphenicol acetyl transferase gene (cat) from Tn9 of E. coli, the beta-glucuronidase gene (gus) of the uidA locus of E. coli, the green, red, or blue fluorescent protein gene, and the luciferase gene. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein.

The recombinant DNA can be readily introduced into the host cells, e.g., mammalian, bacterial, yeast or insect cells, or prokaryotic cells, by transfection with an expression vector comprising the recombinant DNA by any procedure useful for the introduction into a particular cell, e.g., physical or biological methods, to yield a transformed (transgenic) cell having the recombinant DNA so that the DNA sequence of interest is expressed by the host cell. In one embodiment, the recombinant DNA is stably integrated into the genome of the cell.

Physical methods to introduce a recombinant DNA into a host cell include calcium-mediated methods, lipofection, particle bombardment, microinjection, electroporation, and the like. Biological methods to introduce the DNA of interest into a host cell include the use of DNA and RNA viral vectors. Viral vectors, e.g., retroviral or lentiviral vectors, have become a widely used method for inserting genes into eukaryotic cells, such as mammalian, e.g., human cells. Other viral vectors can be derived from poxviruses, e.g., vaccinia viruses, herpes viruses, adenoviruses, adeno-associated viruses, baculoviruses, and the like.

To confirm the presence of the recombinant DNA sequence in the host cell, a variety of assays may be performed. Such assays include, for example, molecular biological assays well known to those of skill in the art, such as Southern and Northern blotting, RT-PCR and PCR; biochemical assays, such as detecting the presence or absence of a particular gene product, e.g., by immunological means (ELISAs and Western blots) or by other molecular assays.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the recombinant DNA segment is being expressed. Expression may be evaluated by specifically identifying the peptide products of the introduced DNA sequences or evaluating the phenotypic changes brought about by the expression of the introduced DNA segment in the host cell.

Vectors for Gene Delivery

Delivery vectors include, for example, viral vectors, liposomes and other lipid-containing complexes, and other macromolecular complexes capable of mediating delivery of a gene to a host cell. Vectors can also comprise other components or functionalities that further modulate gene delivery and/or gene expression, or that otherwise provide beneficial properties. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., WO 92/08796; and WO 94/28143). Such marker genes can provide an added measure of control that can be advantageous in gene therapy contexts. A large variety of such vectors are known in the art and are generally available.

Vectors within the scope of the invention include, but are not limited to, isolated nucleic acid, e.g., plasmid-based vectors which may be extrachromosomally maintained, and viral vectors, e.g., recombinant adenovirus, retrovirus, lentivirus, herpesvirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes. Exemplary gene viral vectors are described below. Vectors may be administered via any route including, but not limited to, intramuscular, buccal, rectal, intravenous or intracoronary administration, and transfer to cells may be enhanced using electroporation and/or iontophoresis.

Peptides, Polypeptides and Fusion Proteins

The peptide or fusion proteins of the invention can be synthesized in vitro, e.g., by the solid phase peptide synthetic method or by recombinant DNA approaches (see above). The solid phase peptide synthetic method is an established and widely used method. These polypeptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, chemically modified derivatives of a given peptide or fusion thereof, can be readily prepared. For example, amides of the peptide or fusion thereof of the present invention may also be prepared by techniques well known in the art for converting a carboxylic acid group or precursor, to an amide. One method for amide formation at the C-terminal carboxyl group is to cleave the peptide or fusion thereof from a solid support with an appropriate amine, or to cleave in the presence of an alcohol, yielding an ester, followed by aminolysis with the desired amine.

Salts of carboxyl groups of a peptide or fusion thereof may be prepared in the usual manner by contacting the peptide, polypeptide, or fusion thereof with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the peptide or fusion thereof may be prepared by utilizing an N-acyl protected amino acid for the final condensation, or by acylating a protected or unprotected peptide, polypeptide, or fusion thereof. O-acyl derivatives may be prepared, for example, by acylation of a free hydroxy polypeptide or polypeptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the polypeptide. Other amino-terminal modifications include aminooxypentane modifications.

In one embodiment, a peptide or fusion protein has substantial identity, e.g., at least 80% or more, e.g., 85%, 90% 95% and up to 100%, amino acid sequence identity to SEQ ID NO:9, 11, 12, 13, or 14, and optionally interferes with the phosphorylation of Nox1, blocks or inhibits binding of NoxA1 activation domain (AD) to Nox1, and/or prevents or inhibits assembly of the p47phox/NoxA1 complex with Nox1 with an efficiency that is reduced, substantially the same, or enhanced relative to SEQ ID NO:9.

Substitutions may include substitutions which utilize the D rather than L form, as well as other well known amino acid analogs, e.g., unnatural amino acids such as α,α-disubstituted amino acids, N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoyl-phenylalanine, phenylglycine, propargylglycine, sarcosine, ε-N,N,N-trimethyllysine, ε-N-acetyllysine, N-acetylserine, N-formylmethionine, 3-methylhistidine, 5-hydroxylysine, ω-N-methylarginine, and other similar amino acids and imino acids and tert-butylglycine.

Conservative amino acid substitutions may be employed—that is, for example, aspartic-glutamic as acidic amino acids; lysine/arginine/histidine as polar basic amino acids; leucine/isoleucine/methionine/valine/alanine/proline/ glycine non-polar or hydrophobic amino acids; serine/threonine as polar or hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting peptide, polypeptide or fusion polypeptide. Whether an amino acid change results in a functional peptide, polypeptide or fusion polypeptide can readily be determined by assaying the specific activity of the peptide, polypeptide or fusion polypeptide.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

The invention also envisions a peptide, polypeptide or fusion polypeptide with non-conservative substitutions. Non-conservative substitutions entail exchanging a member of one of the classes described above for another.

Acid addition salts of the peptide, polypeptide or fusion polypeptide or of amino residues of the peptide, polypeptide or fusion polypeptide may be prepared by contacting the polypeptide or amine with one or more equivalents of the desired inorganic or organic acid, such as, for example, hydrochloric acid. Esters of carboxyl groups of the polypeptides may also be prepared by any of the usual methods known in the art.

The peptides or polypeptides of the invention may be labeled, e.g., with a fluorophore or other detectable moiety, and/or fused to a peptide or polypeptide such as GFP, RFP, BFP and YFP, which may facilitate detection. Labels and peptides which may facilitate detection (or isolation and purification) include but are not limited to a nucleic acid molecule, i.e., DNA or RNA, e.g., an oligonucleotide, a protein, e.g., a luminescent protein, a peptide, for instance, an epitope recognized by a ligand, for instance, maltose and maltose binding protein, biotin and avidin or streptavidin and a His tag and a metal, such as cobalt, zinc, nickel or copper, a hapten, e.g., molecules useful to enhance immunogenicity such as keyhole limpet hemacyanin (KLH), cleavable labels, for instance, photocleavable biotin, a fluorophore, a chromophore, and the like.

Formulations and Dosages

The peptides or fusions thereof, or nucleic acid encoding the peptide or fusion of the invention, can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

The peptides or fusions thereof, or nucleic acid encoding the peptide or fusion, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral administration, the peptides or fusions thereof, or nucleic acid encoding the peptide or fusion, may be combined with one or more excipients and used in the form of ingestible tablets, buccal tablets, troches, capsules, elixirs, suspensions, syrups, wafers, and the like. Such compositions and preparations should contain at least 0.1% of active agent. The percentage of the compositions and preparations may, of course, be varied and may conveniently be between about 2 to about 60% of the weight of a given unit dosage form. The amount of active agent in such useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The peptides or fusions thereof, or nucleic acid encoding the peptide or fusion, may also be administered intravenously or intraperitoneally by infusion or injection. Solutions of the peptides or fusions thereof, or nucleic acid encoding the peptide or fusion or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active agent in the required amount in the appropriate solvent with various of the other ingredients enumerated above, as required, followed by filter sterilization. In the case of sterile powders for the preparation of sterile injectable solutions, the methods of preparation include vacuum drying and the freeze drying techniques, which yield a powder of the active ingredient plus any additional desired ingredient present in the previously sterile-filtered solutions.

For topical administration, the peptides or fusions thereof, or nucleic acid encoding the peptide or fusion, may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the peptides or fusions thereof, or nucleic acid encoding the peptide or fusion, can be determined by comparing their in vitro activity and in vivo activity in animal models. Methods for the extrapolation of effective dosages in mice, and other animals, to humans are known to the art; for example, see U.S. Pat. No. 4,938,949.

Generally, the concentration of the peptides or fusions thereof, or nucleic acid encoding the peptide or fusion, in a liquid composition, such as a lotion, may be from about 0.1-25 wt-%, e.g., from about 0.5-10 wt-%. The concentration in a semi-solid or solid composition such as a gel or a powder may be about 0.1-5 wt-%, e.g., about 0.5-2.5 wt-%.

The amount of the peptides or fusions thereof, or nucleic acid encoding the peptide or fusion required for use alone or with other agents will vary with the route of administration, the nature of the condition being treated and the age and condition of the patient and will be ultimately at the discretion of the attendant physician or clinician.

The peptides or fusions thereof, or nucleic acid encoding the peptide or fusion, may be conveniently administered in unit dosage form; for example, containing 5 to 1000 mg, conveniently 10 to 750 mg, or conveniently 50 to 500 mg of active ingredient per unit dosage form.

In general, however, a suitable dose may be in the range of from about 0.5 to about 100 mg/kg, e.g., from about 10 to about 75 mg/kg of body weight per day, such as 3 to about 50 mg per kilogram body weight of the recipient per day, for example in the range of 6 to 90 mg/kg/day, e.g., in the range of 15 to 60 mg/kg/day.

The invention will be further described by the following non-limiting example.

Example

Materials and Methods

Materials

The following materials were obtained from Sigma-Aldrich: TNF-α (T7539, T0157), Diphenyleneiodoium chloride (DPI, D2926), BME Vitamins (B6891), Trypsin inhibitor (T9128), Lucigenin (M8010), NADPH (100929-71-3). From Calbiochem: CalphostinC (CalC, 208725). From Biorad: 4-20% and AnyKD Gels (456-9033S, 456-1096). From Whatman: Nitrocellulose membranes (10402468). From Invitrogen/Life Technologies: Protein G Dynabeads (10003D), Opti-MEM (11058-021), To-Pro-3 (T3605), CM-H2DCFDA (C6827), RNAiMax (13778), DH5α Max Efficiency competent cells (18258-012), Lipofectamine 2000 (11668-019). From Roche: Protease inhibitor cocktail (1873580). From Fisher Scientific: Permount (SP15-500). From Gibco: PBS (14190), HBSS (14025), DMEM (11965), Phenol red-free DMEM (31053), Pen Strep (15140), L-Glutamine (25030), MEM (11130), HEPES (15630), Trypsin (25200). From Atlanta Biologicals: Fetal Bovine Serum (FBS, S11550). From Vector Laboratories: Vectashield (H-1000), Vectashield plus DAPI (H-1200). From Santa Cruz: siPKC-β (sc-36255). From Ambion: siControl (AM4637). From Qiagen: Taq Polymerase (201203), QIAquick Gel Extraction Kit (28704), QIAquick PCR Purification Kit (28104), Qiagen Plasmid Maxi Kit (12162). From New England Biolabs: ECORI (R0101S), XhoI (R0146S), CIP (M0290S), T4 DNA Ligase (M0202S). The following antibodies were used: pSTY (Phosphoserine/threonine/tyrosine, Abcam ab15556), anti-Nox1 (Sigma SAB2501686 and Santa Cruz sc-5821), anti-FLAG-HRP (Sigma A8592), anti-FLAG (Sigma F1804), anti-p67$^{phox}$ (BD 610912), anti-GAPDH (Millipore MAB374); anti-PKC-βI (Santa Cruz sc-209), PKC-βII (Santa Cruz sc-210), anti-NoxA1 (Abcam ab68523); anti-p22$^{phox}$ (Santa Cruz sc-11712) and anti-p47$^{phox}$ (generously provided by Dr. William Nauseef, University of Iowa).

Animal Models

All procedures were approved by the Institutional Animal Care and Use Committee at University of Iowa and complied with the standards stated in the National Institutes of Health Guide for the Care and Use of Laboratory Animals.

Primate Atherosclerosis:

Frozen aortas from adult male Cynomolgus monkeys fed either a normal or atherosclerotic (AS) diet (0.7% cholesterol and 43% of total calories as fat) for 45 months as described in Stanic et al, (2012) were prepared for immunoprecipitation/Western blotting (IP/WB) as described below.

Rat Balloon Injury:

VSMCs isolated from the medial and neointimal layers of rat aortas following balloon injury as previously described in Xu et al. (2012) were cultured and prepared for IP/WB as detailed below.

Mouse Carotid Ligation:

Carotid ligations were performed in C57B16/J mice as previously described in Chu et al. (2011). Five or 28 days following surgery, carotids were collected and tissues were prepared for IP/WB as detailed below. For IP/WB, for the 5-day time point, tissue from two mice was combined for one ligated and one control sample. For the 28-day time point, tissue from five mice was combined into two samples each for ligated and control samples.

Cultured Cells

Rat aortic medial and neointimal VSMCs were isolated and cultured in 10% Fetal Bovine Serum (FBS) in Dulbecco's Modified Eagles Medium (DMEM) containing 1% BME vitamins, 2 mM glutamine, 10 U/mL penicillin, 10 μg/ml streptomycin, 20 mM HEPES, and 1% MEM non-essential amino acids. Cells were kept at 37° C. and 5% $CO_2$. Wild-type (WT) and $Nox1^{-/y}$ aortic VSMCs were isolated and cultured as above. A7r5 rat aortic vascular smooth muscle cell line from ATCC was cultured as above. CosPhox cells were a generous gift from Dr. Mary Dinauer (Washington University in St. Louis) (Price et al., 2002). These are Cos 7 cells that stably express $p22^{phox}$ or $p22^{phox}$ with $p47^{phox}$ and $p67^{phox}$. These cells are maintained on selective 10% FBS cell culture medium containing 0.2 mg/mL hygromycin, 0.8 mg/mL geneticin, and 1 μg/mL puromycin.

Tissue Preparation

Monkey aorta and mouse carotid tissues were placed in NP40 lysis buffer (1% NP-40, 150 mM $NaCl_2$, 50 mM Tris, 2 mM EDTA, pH 7.2, 4% protease inhibitor cocktail, 1 mM sodium vanadate and 1 mM sodium fluoride are added fresh) on ice, and homogenized using a Tissue Tearor (Biospec Products, model 985370). Cultured cells were washed in PBS, lysed with NP40 lysis buffer, and scraped into microcentrifuge tubes. All samples were centrifuged at 1000 g for 5 minutes at 4° C., sonicated twice for 10 seconds at 10 Watts at 4° C., centrifuged at 5000 g for 10 m at 4° C., and supernatant (SNT) was transferred to new tubes on ice. Protein concentrations were measured by Bradford assay, and concentrations of samples were normalized by addition of NP40 lysis buffer. Samples were then subjected to IP as detailed below.

Immunoprecipitation

Equal volumes of samples were pre-cleared with Protein G Dynabeads (10 μL/1.5 mg protein in lysate) for 30 minutes at 4° C., end-over-end rotation, followed by a quick spin at high speed, then placed on a magnetic rack for 1 minute. SNT was removed to a new tube on ice. The $p22^{phox}$/Nox1 complex was immunoprecipitated using anti-$p22^{phox}$ antibody C-17 (1 μg/500 μg protein in lysate) and rotated for 45 minutes at 4° C. (Hanna et al., 2004). Next, 20 μL Protein G Dynabeads was added to each sample and rotated for 20 minutes at 4° C., followed by a quick spin at high speed, then placed on a magnetic rack 1 m. SNT was moved to a new tube on ice and frozen for later analysis. The Dynabead pellet was washed three times with 200 μL NP40 buffer, followed by addition of 15 μL twice with sample buffer (4% SDS, 20% glycerol, 10% 2-mercaptoethanol, 0.004% bromphenol blue, 0.125 M Tris HCl, pH 6.8). Samples were shaken in an orbital shaker for 30 m. Samples were then analyzed by WB.

Western Blotting

Figure 7:
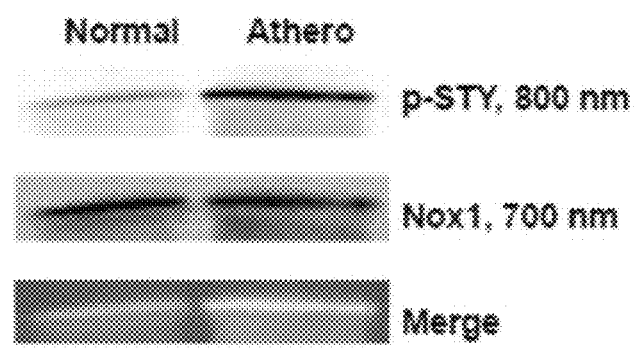
FIG. 7. Co-localization of Nox1 and phosphoserine/threonine/tyrosine (p-STY) signals by Odyssey imaging. Monkey carotid homogenates were immunoprecipitated using p22$^{phox}$ antibody to pull down the Nox1/p22$^{phox}$ complex. Immunoprecipitates were subjected to SDS-PAGE, transferred to nitrocellulose, and probed with Nox1 (goat) antibody and p-STY (mouse) antibody, followed by incubation in infared secondary antibodies detected by the Odyssey imaging system: anti-mouse 800 green (upper), anti-goat 700 red (middle), and merged image (lower).

One quarter volume of 5× sample buffer (6 g SDS, 40% glycerol, 30% 2-mercaptoethanol, 383.3 mg dithiothreitol, 372 mg EDTA, 378.3 mg Tris, 50 mg bromphenol blue in 50 ml $ddH_2O$, pH 6.8) was added to lysates. All samples were mixed in an orbital shaker for 30 minutes at 250 rpm. Samples were run on 4-20% or AnyKD gels @ 200 Volts for about 30 minutes, transferred to nitrocellulose membranes for 45 minutes at 100 Volts. Membranes were blocked in 3% BSA TBS (for Odyssey imaging) or 5% BSA TBS-T (for Kodak imaging) 1 hour rocking, then probed with primary antibodies for 1 hour or overnight at 4° C., then washed in 1% BSA TBS-T five times for 5 minutes, then probed with appropriate infrared secondary antibody, washed twice for 5 minutes in N-TBS, washed once with TBS and imaged by Odyssey. Anti-Flag-HRP was developed with a West-Femto kit (Thermo-Scientific) and imaged on a Kodak Image Station 4000R. Phosphorylation of Nox1 residues was determined utilizing a phospho-serine/threonine/tyrosine (p-STY) antibody that reacts with these residues only under phosphorylated conditions (Zhang et al., 2010, Chen et al., 2006). This value was normalized to total Nox1. Utilization of two infrared secondary antibodies (with emissions at 700 or 800 nm) and Odyssey imaging allowed the visualization of both probes simultaneously to confirm that the phospho-signal corresponded with Nox1 (FIG. 7).

Nox1 Phosphorylation in VSMCs

C57 VSMCs were either pre-treated with Calphostin C (CalC), or an equivalent volume of DMSO (vehicle). CalC was mixed to a final concentration of 100 nM in cell culture medium lacking FBS, added to cells, light activated for 10 minutes, incubated at 37° C. in dark for 20 minutes, prior to addition of agonist. Cells were then treated with 10 ng/mL mouse TNF-α for 10 minutes at 37° C., washed three times in cold HBSS, lysed in NP40 lysis buffer and prepared for IP/WB.

ROS Detection by Fluorescence

C57 WT or $Nox1^{-/y}$ VSMCs were seeded on glass chamber slides at 75% confluence, serum-starved in cell culture medium containing no FBS for 24 h, washed in phenol red-free DMEM, and incubated in 10 μM CM-H2DCFDA for 30 m, pretreated with CalC or DMSO, and treated with 10 ng/mL TNF-α for 30 minutes. The cells were then washed 3×100 μL cold PBS, fixed with 2% paraformaldehyde for 15 minutes, washed twice with PBS, incubated in 1 μM To-Pro-3 for 5 minutes in dark, and washed twice with PBS. The chambers were removed and cells were mounted in Vectashield and imaged by confocal microscopy.

ROS Detection by Lucigenin-Enhanced Chemiluminescence

A7r5 rat aortic smooth muscle cells were seeded at 75% confluence in 10% FBS medium, infected with AdNox1GFP for 48 hours, serum-starved in 0.2% FBS medium for 24 hours. Cells were then subjected to a 30 minute pre-incubation with 100 nM DPI or 100 μM CalC or DMSO, then treated with 10 ng/mL TNF-α for 10 minutes, washed three times in cold PBS, and homogenized in Homogenization Buffer (0.25 M sucrose, 10 mM triethanolamine, 4% protease inhibitor cocktail, 0.1 M EDTA, pH 7.4) with a Tissue Tearor. Lucigenin was then added to a final concentration of 5 μM. Samples were then analyzed by a FB12 Chemiluminometer every 10 seconds for 5 minutes. Then NADPH was added to a final concentration of 100 μM and readings were taken for another 5 m. Average baseline value was subtracted from the average NADPH-stimulated value.

For CosPhox cells, following either mock transfection or transfection with wild-type or mutant Nox1, membrane fractions were prepared and assayed for ROS detection by lucigenin-enhanced chemiluminescence as above.

Membrane Fraction Preparation

Following serum starvation, cells were treated with 2 mL 20 ng/mL TNF-α in FBS-free medium or treated with FBS-free medium alone at 37° C. for 10 minutes. Plates were then placed on ice, washed three times with cold HBSS, and lysed in 150 µL NP40 lysis buffer. Cells were scraped and transferred to a tube on ice, centrifuged at 1000 g for 5 minutes at 4° C., sonicated twice for 10 seconds at 10 Watts, and centrifuged at 5000 g for 10 minutes at 4° C. Supernatants (SNT) were transferred to new tubes on ice. The SNT was centrifuged at 16,000 g for 30 minutes at 4° C. The SNT from this spin was transferred to a Beckman polycarbonate thick-walled ultracentrifuge tube and centrifuged at 100,000 g for 1 hour at 4° C. The SNT from this spin was aspirated and the pellet was resuspended in 100 µL NP40 buffer.

Migration Assay

WT or Nox1$^{-/y}$ C57 mouse aortic VSMCs were pretreated with CalC or DMSO (vehicle) for 30 minutes, washed once with PBS, and cells were detached with trypsin, which was quenched with trypsin inhibitor. Cells were transferred to a conical tube, centrifuged at 500 g for 5 minutes. The SNT was aspirated, and cells were resuspended in 125 µL cell culture medium containing no FBS. Cell counts were obtained on a Beckman Z1 Coulter Particle Counter. Cells suspensions were diluted to a concentration of 1,000 cells/µL. 50 µL of the cell suspension was added to the upper chamber of a Costar Transwell Permeable Support (8.0 µm polycarbonate membrane, 6.5 mm insert). 500 µl medium containing no FBS with or without TNF-α was added to the lower chamber. Chambers were incubated for 5 hours at 37° C. Medium was aspirated, Transwells were washed twice with PBS, non-migrated cells were removed from the upper surface of the membrane with a cotton swab, followed by washing twice with PBS. Cells were fixed in 4% paraformaldehyde, membranes were removed from support with a scalpel and mounted in Vectashield plus DAPI, coverslipped and five random fields from each membrane were imaged at 20× and the number of cells migrated to the bottom of the Transwell was counted. Data are reported as average number of cells per field after subtracting the number of cells that migrated under unstimulated conditions for each group.

Mass Spectroscopy

Human aortic VSMCs were treated with TNF-α, cells were lysed and the lysate was subjected to IP with anti-p22$^{phox}$ antibody. The IP was then subjected to SDS-PAGE to separate proteins. The gel was stained with Coomassie blue and bands were excised and subjected to MALDI-TOF mass spectroscopy.

siPKC-β

500 µL Opti-MEM was added to a 60 mm gelatin-coated cell culture plate. To this siPKC-β or siControl was added (final concentration 200 nM), plus 12 µL RNAiMax. Plates were rocked and incubated for 20 minutes. Cells were detached by use of trypsin, which was quenched in 10% FBS containing no antibiotics, centrifuged at 500 g for 5 minutes, resuspended in 5 mL 10% FBS without antibiotics and counted. Cells were added to plate for a seeding density of 75%, and medium was added to a final volume of 3 mL. Cells were incubated for 5 hours at 37° C., then medium was changed to 10% FBS. The next day, cells were serum starved in medium containing no FBS for 24 hours. Cells were then prepared for analysis by WB, DCF fluorescence or migration assay.

Nox1 Mutant Constructs pcDNA3.1 containing rat Nox1 (kindly provided by Dr. Kathy Griendling, Emory University) was used as a template for generating the Nox1 mutant constructs using the following primers:

Nox1T89A-F:
(SEQ ID NO: 1)
5'-GCT-CAT-TTT-GCA-ACC-ACG-CGC-TGA-GAA-AGC-CAT-TG-3',

Nox1T89A-R:
(SEQ ID NO: 2)
5'-CAA-TCC-CTT-TCT-CAG-CGC-GTG-GTT-GCA-AAA-TGA-GC-3',

Nox1T429A-F:
(SEQ ID NO: 3)
5'-CGT-GCA-CAC-AAC-AAG-CTG-AAA-GCA-CAA-AAG-ATC-TAT-TTC-TAC-3',

Nox1T429A-R:
(SEQ ID NO: 4)
5'-GTA-GAA-ATA-GAT-CTT-TTG-TGC-TTT-CAG-CTT-GTT-GTG-TGC-ACG-3',

Nox1T429D-F:
(SEQ ID NO: 5)
5'-CGT-GCA-CAC-AAC-AAG-CTG-AAA-GAC-CAA-AAG-ATC-TAT-TTC-TAC-3',

Nox1T429D-R:
(SEQ ID NO: 6)
5'-GTA-GAA-ATA-GAT-CTT-TTG-GTC-TTT-CAG-CTT-GTT-GTG-TGC-ACG-3'.

Constructs were generated using the QuikChange II Site-Directed Mutagenesis Kit (Stratagene #200523) or QuikChange Multi Site-Directed Mutagenesis Kit (Stratagene #200514) according to manufacturer's instructions.

DNA was sequenced using the Applied Biosystems Model 3730 to ensure mutations were present at correct locations.

Flag Tagging Constructs

Wildtype Nox1 constructs were modified to include a C-terminal Flag tag by using PAGE purified primers, Forward-5'-GAATTCCCTGGAACAAGAGATGGACGAATT-AGGCAA-3' (SEQ ID NO:7) Reverse-5'-CAACTCCTC-GAGTCACTTATCGTCGTCATCCTTGTAATCG AACGTTTCTTT GTTGAAGTAGAATT-3' (SEQ ID NO:8) which included the EcoRI and XhoI restriction sites using Taq Polymerase. The amplified region was gel purified using the QIAquick Gel Extraction Kit. The original constructs and the amplified region which included the Flag tag were digested with EcoRI and XhoI at 37° C. for 3 hours. The original constructs that had been cut were then dephosphorylated using CIP for 1 hour at 37° C. Both the dephosphorylated vector and amplified regions were cleaned up with the QIAquick PCR Purification Kit. The two products were ligated with T4 DNA Ligase at 16° C. overnight. The reaction was transformed in to DH5a Max Efficiency competent cells, plated on LB-Agar ampicillin plates and grown overnight at 37° C. Colonies were picked, grown in LB overnight and the DNA was isolated the following day using the Qiagen Plasmid Maxi Kit. The presence of the Flag tag was confirmed by sequencing using the Applied Biosystems Model 3730.

CosPhox Cell Transfection

On day 1, cells were seeded in 60 mm cell culture plates at 55% confluence. Day 2, cells were transfected with 4 µg DNA and 12 µL Lipofectamine 2000. Opti-MEM with 50 mM CaCl$_2$ was used for transfections. 4 µg DNA was added to 400 µL and 12 µL Lipofectamine 2000 was diluted in 400 µL for 10 minutes. These were mixed and allowed to incubate for 30 minutes. An additional 1.2 mL was added for a final volume of 2 mL per transfection solution for each construct per plate. Cells were incubated for 4 hours, aspirated, washed once in 10% FBS medium, and incubated in 2 mL 10% FBS medium overnight. Day 3, cells were serum starved in cell culture medium containing no FBS for 48 hours. In some experiments (FIG. 6C), cells that contained only $p22^{phox}$ were co-transfected with $p47^{phox}$ and NoxA1 (kindly provided by Dr. Botond Banfi, University of Iowa) at the time of Nox1 transfection.

VSMC Transfection

Figure 12:
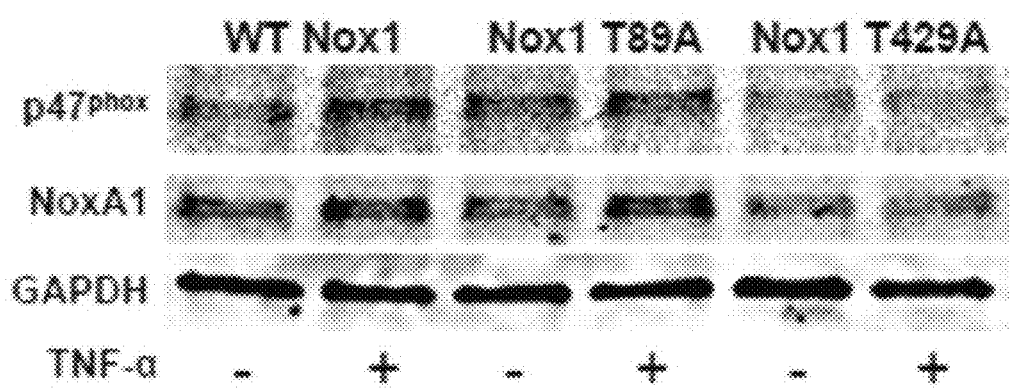
FIG. 12. Role for Nox1 T429 in recruitment of p47$^{phox}$ and NoxA1 to the membrane. Nox1$^{-/y}$ VSMCs were transfected with WT or mutant Nox1, p22$^{phox}$, p47$^{phox}$, and NoxA1. Cells were treated with TNF-α, and then membrane fractions isolated and blotted for p47$^{phox}$ or NoxA1. Whole cell lysates (prior to membrane isolation) were probed with anti-GAPDH as the loading control.

On day 1, 4 μg DNA, 7.07 μL Plus Reagent, and 17.66 μl Lipofectamine LTX were incubated in 5.625 ml Optimem for 30 minutes. Meanwhile, VSMCs were trypsinized, and trypsin was quenched with 10% FBS cell medium without antibiotics. The appropriate volume of cells was added to the DNA mixture in order to achieve 75% cell density per 60 mm cell culture plate. After 4 hours, the DNA mix was aspirated and cells were serum starved in cell culture medium containing no FBS for 48 hours. In some experiments (FIG. 12), cells were co-transfected with $p22^{phox}$, $p47^{phox}$, and NoxA1 (kindly provided by Dr. Botond Banfi, University of Iowa) at the time of Nox1 transfection.

Complex Assembly Assay

Cells were treated with 10 ng/mL TNF-α for 10 minutes. Cells were then lysed, membrane fractions were prepared, and samples were analyzed for recruitment of $p47^{phox}$ and NoxA1 to the membrane fraction by WB.

Isothermal Titration Calorimetry In Vitro Kinase Assay

The ability of PKC-βI to phosphorylate threonine 429 on Nox1 was assessed by ITC using the single injection method described by Gomez (2001). For these experiments, the unphosphorylated Nox1 peptide was resuspended in a buffer containing 20 mM $Na_2HPO_4$, 100 mM $NaCl_2$, pH 7.4. The Nox1 peptide was diluted to a concentration of 1 mM and the PKC-βI was diluted to a concentration of 10 fM in a buffer containing 20 mM HEPES, 10 mM $MgCl_2$, 3 mM $CaCl_2$, 1 mM DTT, 5 μg/mL diacylglycerol, 10 mM ATP, 150 μg/mL phosphatidylserine. The peptide and protein solutions were degassed and ITC measurements were recorded using a MicroCal VP-ITC System. 30 μL injections of Nox1 peptide into the PKC-βI solution were performed with 30 minute spacing between events. The chamber was kept under constant stirring at 350 rpm and all experiments were performed at 25° C.

Isothermal Titration Calorimetry Peptide Interaction

The affinity of the interaction between non-phosphorylated and phosphorylated Nox1 and NoxA1 was determined by isothermal titration calorimetry (ITC). Phosphorylated or non-phosphorylated peptides corresponding to amino acids KLKTQKIYF (SEQ ID NO:9) of Nox1 and a peptide corresponding to amino acids LEPMDFLGKAKVV (SEQ ID NO:10) of NoxA1 peptides were purchased from ProImmune. The peptides were resuspended in 20 mM $Na_2HPO_4$, 100 mM $NaCl_2$, pH 7.4 to a final concentration of 800 μM (Nox1) and 20 μM (NoxA1). The peptides were degassed and ITC measurements recorded using a MicroCal VP-ITC System (GE Healthcare). 21 injections of Nox1 peptides into NoxA1 peptide were used, with 240 s spacing between events. The chamber was kept under constant stirring at 350 rpm and all experiments were performed at 25° C. Control experiments where Nox1 peptides were injected into buffer showed that the heats of dilution were constant across all injections. The constant heat of dilution, as determined by the average of the last 3-5 injections, was subtracted and the data are analyzed using the single site binding model provided in the ITC analysis package. The values for affinity and stoichiometry from three experiments were averaged and shown±standard deviation.

Dot Blot

Nitrocellulose membranes measuring 1 $cm^2$ were placed in a 96-well plate, incubated in 100 μL, kinase assay input, product, or 1 mM Nox1 phospho-peptide solution in duplicate and allowed to dry overnight. One set of membranes were then incubated for 1 hour in 300 μL, Odyssey Blocking Buffer, 1 hour in 300 μL, p-STY antibody solution (1:100 in Odyssey Blocking Buffer), washed 5 times for 5 minutes in 300 μL, TBS with 1% NP40, incubated 1 hour in 300 μL, secondary antibody solution (Licor infrared 680 1:1000 in Odyssey Blocking Buffer), washed 5 times for 5 minutes in 300 μL, TBS with 1% NP40. The other set of membranes were incubated in Ponceau stain for 5 minutes and washed 5 times in $ddH_2O$. All membranes were imaged by Odyssey.

Computer Modeling

A homology model of the rat cytosolic C-terminal FAD-NADPH binding domain (residue 290-563 NP446135.1) was generated using the hm_build.mer macro in Yasara Structure 13.1.5 (see www.yasara.org). The highest scoring templates used by Yasara were the cytochrome B5 reductase crystal structure (PDB ID 2EIX) for the FAD domain and the Nox2 crystal structure (PUB ID 3A1F) for the NADPH domain. A phosphorylated T429 version of the Nox1 cytosolic C-terminal domain was also generated and both homology models energy minimized using the NOVA force field in Yasara. Docking of the NoxA1 AD peptide to the homology models generated above was performed using the AutoDock Morris et al., (1998) derivative implemented in Yasara. The docked poses were visualized and ray-traced in PyMOL 1.6 (Schrödinger), Circular Dichroism CD analysis was performed to investigate secondary structure of a Nox1 peptide containing T429 in a non-phosphorylated (KLKTQKIYF; SEQ ID NO:9) or phosphorylated (KLK-phospho-T(429)QKIYF) state. CD analysis was also performed on the NoxA1 AD peptide individually and in a 1:1 complex with the Nox1 peptides. The peptides were prepared in buffer containing 20 mM $Na_2HPO_4$, 100 mM $NaCl_2$, pH 7.4. CD spectra were collected on 100 μM samples in a 1-mm cuvette at 25° C. over the range of 190-250 nm with an interval of 1 nm and a scan speed of 100 nm/m using a Jasco J-815 CD spectrophotometer.

Statistical Analysis

Results are expressed as mean±SEM. Statistical comparisons were performed by one-way or two-way analysis of variance (ANOVA) with appropriate post-hoc analysis. A p value of <0.05 was considered significant.

Results

Nox1 Phosphorylation is Increased in Multiple Models of Vascular Disease

Phosphorylation is a common mechanism for post-translational regulation of protein activity. Using an antibody that detects phosphorylation at serine, threonine and tyrosine residues (anti-STY), it was examined whether Nox1 is phosphorylated under conditions known to be associated with increased Nox1 activity. Specifically, anti-$p22^{phox}$ immunoprecipitation was used for and subjected to Western Blotting with anti-STY or anti-Nox1 in three models of vascular disease. First, increased levels of Nox1 phosphorylation were detected in aorta from monkeys fed an atherogenic diet as compared to normal diet (FIG. 1A, FIG. 7). Next, elevated Nox1 phosphorylation was found in cultured VSMCs derived from the neointima of balloon-injured rat aorta as compared to medial VSMCs (FIG. 1B). Using a murine carotid injury model known to induce neointimal hyperplasia, Nox1 phosphorylation was significantly increased as compared to contralateral non-injured arteries (FIG. 1C). These results provide evidence of Nox1 phosphorylation in response to vascular injury.

Nox1 is Activated by Protein Kinase C-131 Phosphorylation

Figure 2:
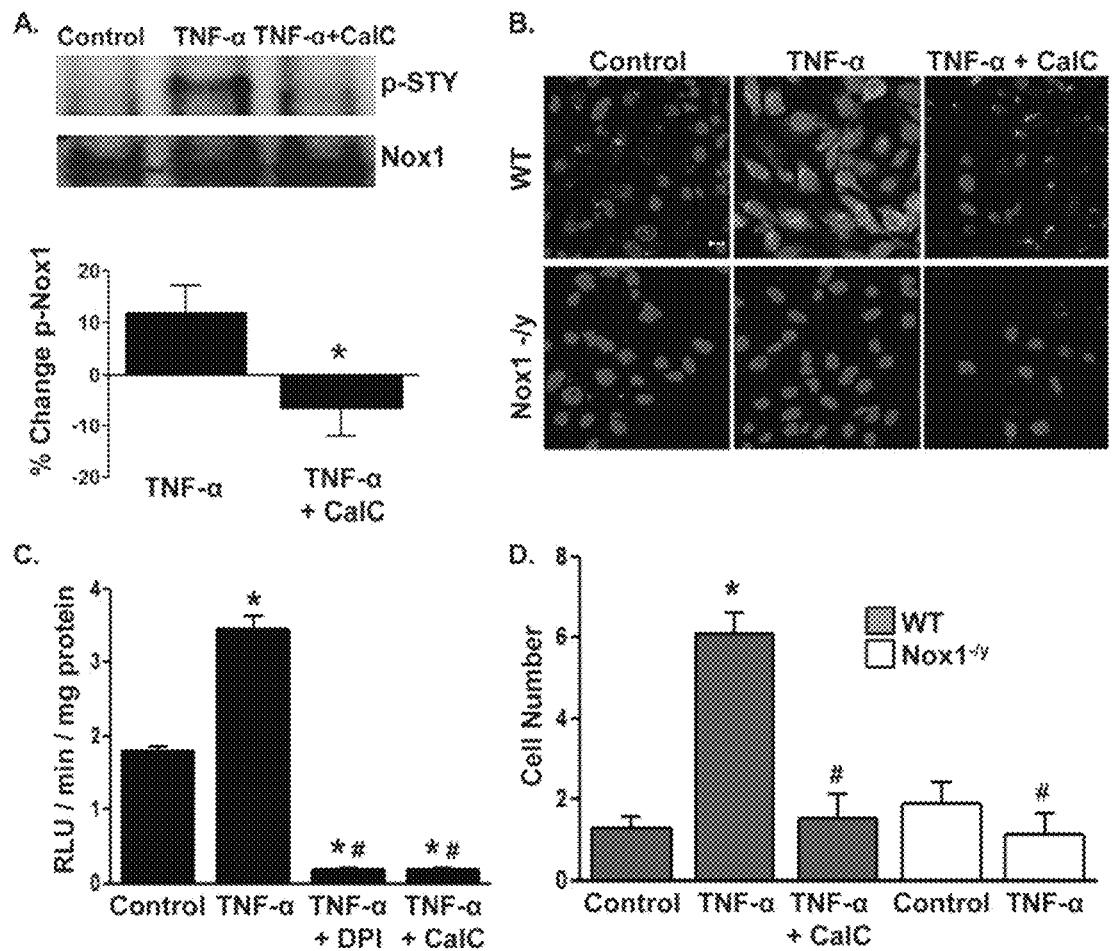
FIG. 2. PKC inhibition abolishes TNF-α-mediated Nox1 phosphorylation, ROS production and VSMC migration. The effect of Calphostin C (CalC) pretreatment on TNF-α-mediated (A) Nox1 phosphorylation in rat VSMCs by Western blotting with anti-STY as in FIG. 1, (B) CM-H$_2$DCF fluorescence (green) in murine VSMCs, (C) lucigenin-enhanced chemiluminescence (RLU: relative light units) in rat VSMCs, and (D) migration of murine VSMCs. In (B), nuclei were counterstained with ToPro3; scale bar=10 μm. n=3 in A and 5-15 in C, D. *$p<0.05$ vs. control, #$p<0.05$ vs. WT TNF-α-treated.

Next, NetPhosK sequence analysis software was used to identify putative kinases that phosphorylate Nox1. Of the top 10 predicted phosphorylation sites, protein kinase C was the predicted kinase for 7 of those sites (FIG. 8). Therefore, it was examined whether inhibition of PKC with Calphostin C (CalC) (Kobayashi et al., 1989) modifies Nox1 phosphorylation following stimulation with TNF-α, which is a known activator of Nox1 (Miller et al., 2007; Miller et al., 2010). Treatment of cultured A7r5 rat aortic VSMCs with TNF-α increased Nox1 phosphorylation (FIG. 2A) similar to levels seen in vivo (FIG. 1). CalC inhibited TNF-α-stimulated Nox1 phosphorylation. Next, TNF-α caused robust ROS production in WT but not Nox1$^{-/y}$ VSMCs (FIG. 2B), confirming that the TNF-α-dependent generation of ROS is Nox1-dependent (Miller et al., 2007; Miller et al., 2010). CalC abrogated Nox1-dependent ROS production in WT VSMCs (FIG. 2B). Analysis of VSMC membrane fractions from WT cells demonstrated that TNF-α pretreatment primes NADPH oxidase activity (FIG. 2C). This effect was completely abolished by either the flavoenzyme inhibitor DPI or CalC (FIG. 2C). Thus, PKC activity is required for Nox1 generation of ROS.

Nox1 has been implicated in VSMC migration to multiple agonists (Le et al., 2009; Jagadeesha et al., 2012; Zimmerman et al., 2011; Schroeder et al., 2007). Using Nox1$^{-/y}$ VSMCs, it was established that VSMC migration to TNF-α requires Nox1 (FIG. 2D). Similar to the effects of PKC inhibition on ROS production, migration of WT VSMCs was blocked with CalC (FIG. 2D). Taken together, these data demonstrate that PKC is necessary for TNF-α-mediated redox-dependent migration.

Figure 3:
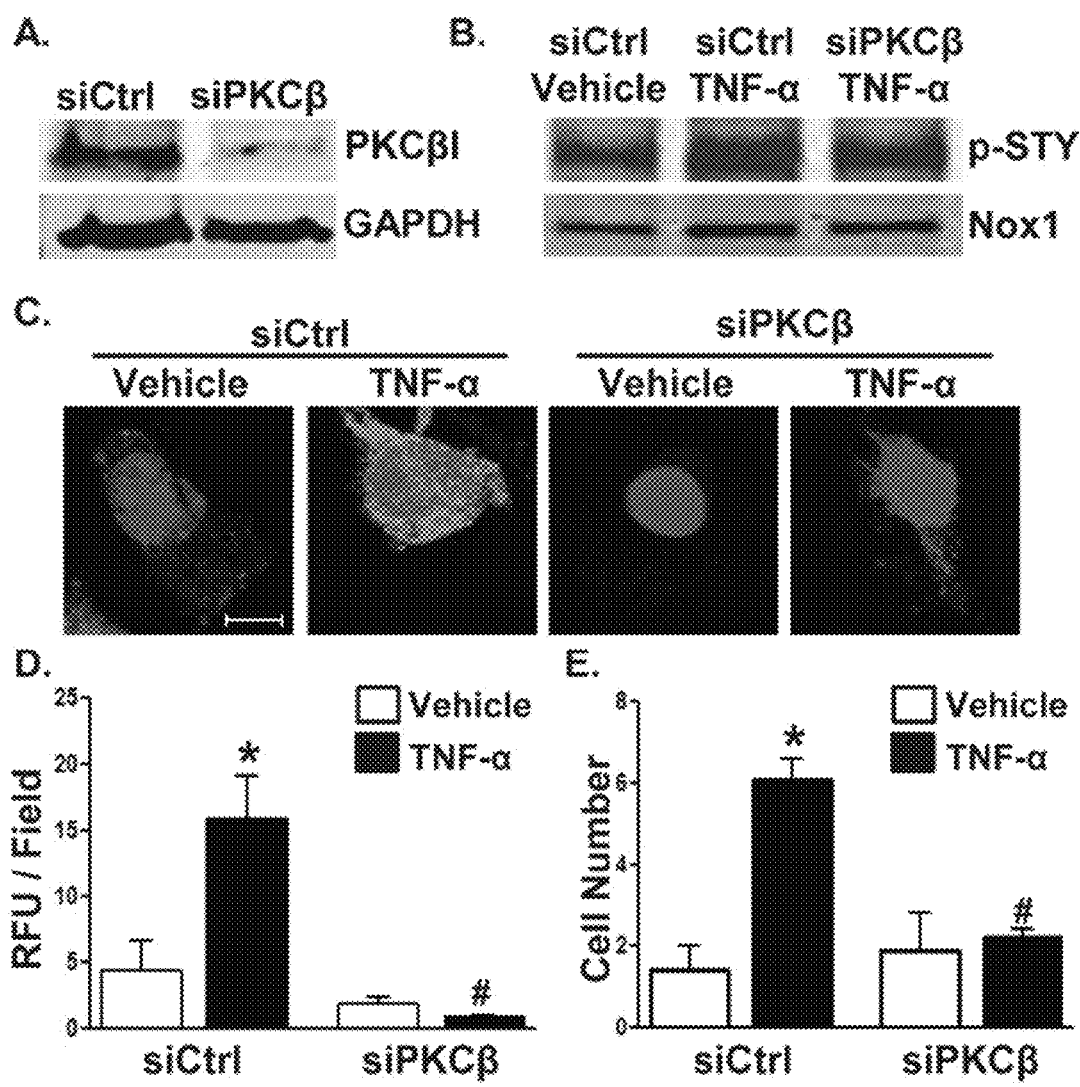
FIG. 3. Knockdown of PKCβ prevents TNF-α-mediated VSMC activation. (A) Validation of PKCβI silencing at the protein level. WT murine VSMCs were treated with control (Ctrl) or PKCβ siRNA followed by treatment with TNF-α and assessment of (B) Nox1 phosphorylation (C,D) CM-H$_2$DCF fluorescence (RFU: relative fluorescent units; n=4-7; scale bar=10 μm), and (E) migration (n=10-15) as in FIG. 2. In (C), nuclei were counter-stained with ToPro3 (blue). *$p<0.05$ vs. vehicle; #$p<0.05$ vs. siCtrl TNF-α-treated.
Figure 9:
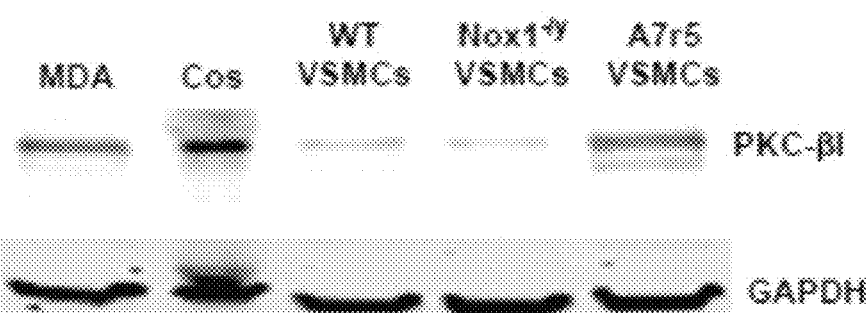
FIG. 9. Analysis of PKC-βI and II expression in VSMC. (A) PKC-βI and (B) PKC-βII protein expression was assessed by Western blotting in cell lysates from CosPhox cells (Cos), C57 mouse aortic vascular smooth muscle cells (VSMCs) from wild-type (WT) and Nox1$^{-/y}$ mice, and A7r5 rat vascular smooth muscle cell line. MDA MB 231 (MDA) breast cancer cell lysate was used as a positive control in (A) and (B). C57 mouse aorta and femoral artery tissue lysates were used as positive controls in (B). GAPDH, loading control.
Figure 9:
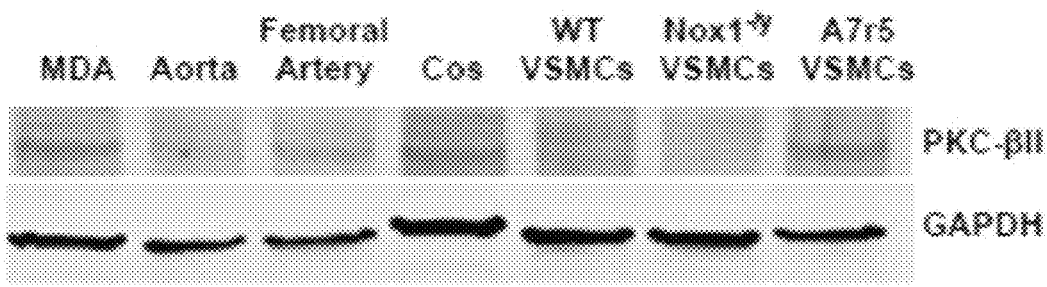

Mass spectrometry identified the interaction of PKC-βI with the Nox1-p22$^{phox}$ complex in response to TNF-α treatment of VSMCs (data not shown). PKC-βI and II are splice variants from the same gene and are both reported to be expressed in mice and humans (Kubo et al., 1957). Western blotting demonstrated expression of PKC-βI but not PKC-βII in WT VSMCs (FIG. 9). Using an siRNA against PKC-β (siPKC-β), significant knockdown of PKC-βI expression was achieved in WT VSMCs (FIG. 3A). Silencing PKC-β resulted in partial inhibition of TNF-α-induced Nox1 phosphorylation (FIG. 3B) and near complete abrogation of ROS production (FIG. 3C), NADPH oxidase activity (FIG. 3D), and VSMC migration (FIG. 3E). These finding suggest that PKC-βI is the kinase that regulates Nox1 NADPH oxidase activation.

PKC-βI Phosphorylation of T429 is Necessary for Nox1 Activation

Figure 4:
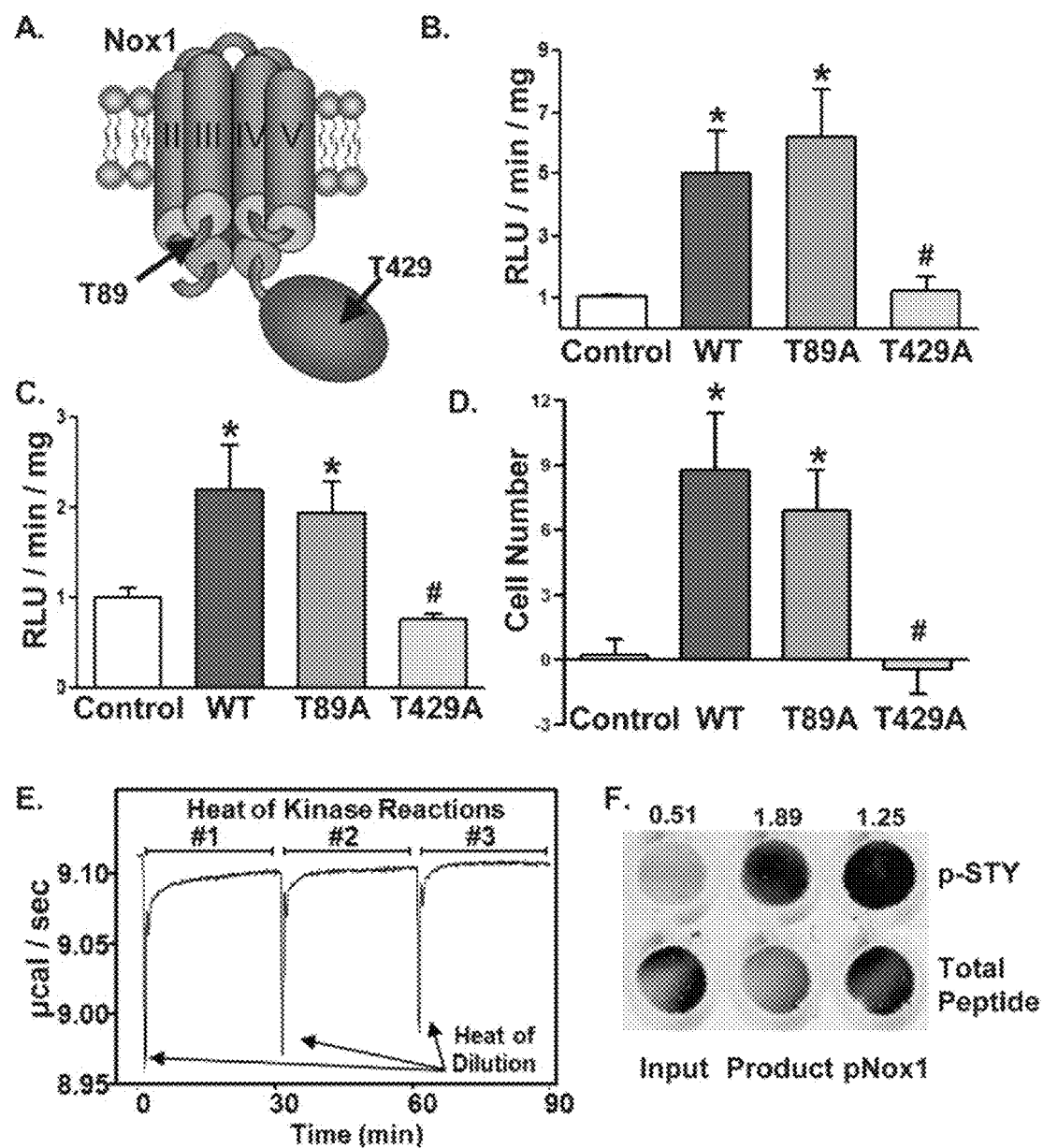
FIG. 4. Nox1 phosphorylation of T429 by PKCβ1 is required for TNT-α-induced ROS production and VSMC migration. (A) Relative locations of T89 and T429 in Nox1. (B) CosPhox cells or (C) Nox1$^{-/y}$ VSMCs expressing the indicated Nox1 mutants were treated with TNF-α, followed by measurement of ROS in membrane fractions by lucigenin-enhanced chemiluminescence. n=3 independent experiments. (D) Migration of Nox1$^{-/y}$ VSMCs expressing the indicated Nox1 mutants to TNF-α. The number of cells migrating under non-stimulated conditions was subtracted from TNT-α-stimulated migration for each group. n=5-10 independent experiments. *$p<0.05$ vs. mock-transfected (control) cells. (E) ITC measurement of in vitro kinase reaction of recombinant PKC-βI with Nox1 peptide (KLK TQKIYF, SEQ ID NO:9. "LocKiT"). (F) To confirm PKC-βI phosphorylation of the Nox1 peptide, dot blot analysis of in vitro kinase assay input and product was performed using anti-p-STY. Phosphorylated Nox1 peptide (pNox1, KLK T*QKIYF). Total peptide levels were determined by Ponceau staining. Data were quantitated as the ratio of p-STY to total peptide using Odyssey imaging software and are indicated above the dot blot.
Figure 10:
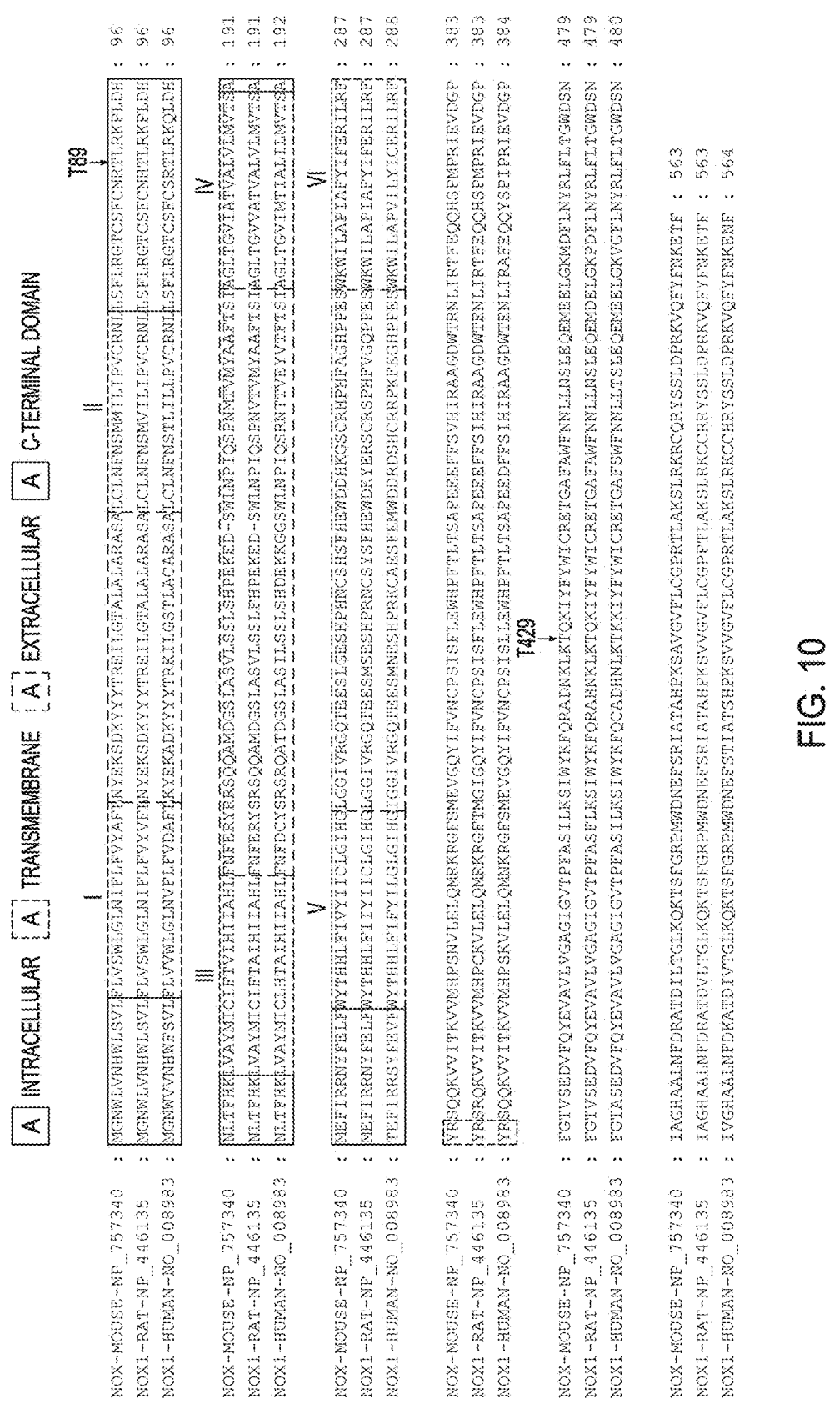

NetPhosK prediction algorithm identified several PKC consensus phosphorylation sites in Nox1 (FIG. 8). Based on the NetPhosK score, the conservation of the putative phosphorylation sites between mouse, rat, and human (FIG. 10), and their location within intracellular regions (FIG. 10 and FIG. 4A), T89 and T429 were evaluated. T89 is located in the first intracellular loop between transmembrane domains I and II, whereas T429 is in the C-terminal region (FIG. 4A).

Figure 11:
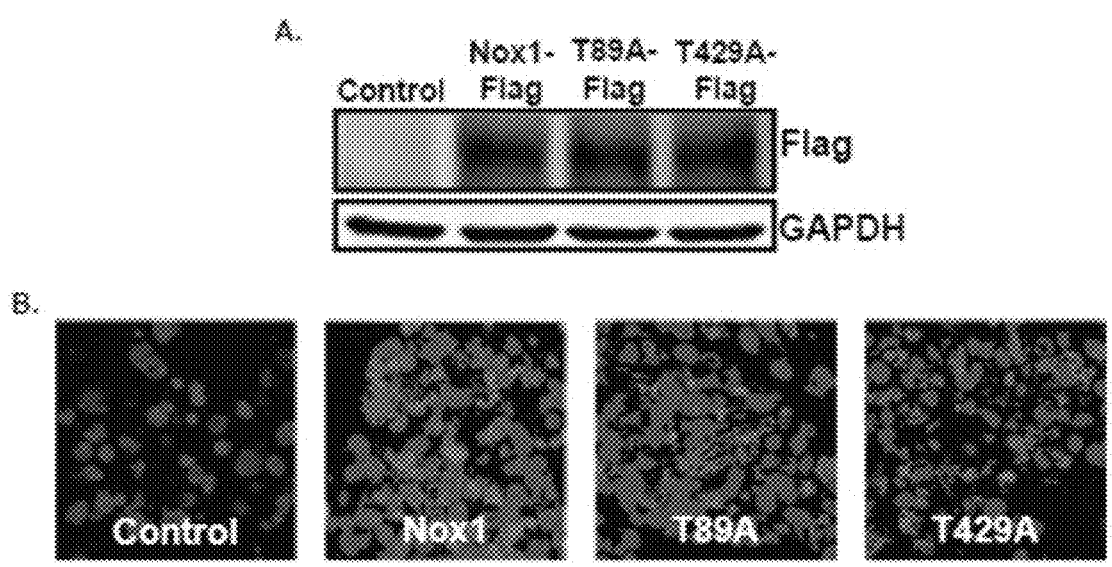
FIG. 11. Validation of Nox1 mutant protein expression in (A) CosPhox cells and (B) Nox1$^{-/y}$ VSMCs. (A) Expression of flag-tagged Nox1 mutants was examined by blotting CosPhox cell lysates with anti Flag. GAPDH, loading control. (B) Expression of flag-tagged Nox1 mutants in Nox1$^{-/y}$ VSMCs was examined by immunofluorescence using anti-Flag primary antibody followed by anti-mouse Alexa Fluor568 secondary antibody (red); nuclei were counter-stained with ToPro3 (blue).

T89 and T429 were mutated to alanine to prevent phosphorylation and it was confirmed that the mutation does not disrupt protein expression. Using Flag-tagged constructs (T89A, T429A, or WT Nox1), expression was validated by Western blotting and immunofluorescence in CosPhox cells that express p22$^{phox}$, p47$^{phox}$, and p67$^{phox}$ but lack Nox1, (Ambasta et al., 2006) and in Nox1$^{-/y}$ VSMCs, which express p22$^{phox}$, p47$^{phox}$, and NoxA1 (Price et al., 2002) (FIG. 11). However, functional analysis demonstrated that the C-terminal epitope tag interfered with ROS production by WT Nox1 (data not shown). Thus, subsequent studies utilized non-tagged Nox1 mutants.

Next, it was examined whether Nox1 phosphorylation at T89 or T429 is required for Nox1 NADPH oxidase activity following TNF-α stimulation. Expression of WT Nox1 in CosPhox (FIG. 4B) or Nox1$^{-/y}$ VSMCs (FIG. 4C) resulted in the anticipated NADPH-stimulated superoxide production as measured by lucigenin-enhanced chemiluminescence in membrane-enriched fractions. Whereas superoxide production in cells expressing T89A Nox1 was similar to WT levels, expression of T429A Nox1 returned superoxide to control levels. Next, it was determined whether T429 is also required for TNF-α-induced VSMC migration. As with superoxide production, migration was similar in Nox1$^{-/y}$ VSMCs expressing either WT or T89A Nox1 (FIG. 4D). By contrast, no migration was observed in cells transfected with T429A Nox1. In addition, expression of a phosphomimetic T429D Nox1 mutant restored migration to 59% of that observed with WT Nox1. These data are consistent with a negative charge at T429 as necessary for Nox1 enzyme activity and VSMC migration following stimulation with TNF-α.

To directly evaluate whether T429 Nox1 is a bona fide PKC-βI phosphorylation site, an in vitro kinase assay was performed using human recombinant PKC-βI and a Nox1 peptide containing T429 (KLK<u>T</u>QKIYF). Isothermal titration calorimetry (ITC) was used to measure the heat generated by phosphorylation of the peptide. The slope of the reaction following the heat of dilution confirms that the Nox1 peptide is a substrate for PKC-βI (FIG. 4E). The reduction in heat produced in subsequent reactions suggests product inhibition, that is inhibition of PKC-βI by the phosphorylated Nox1 peptide (FIG. 4F). This substantial product inhibition precluded measurement of kinetic parameters (Todd and Gomez, 2001). In addition, dot blot analysis of the kinase reaction using p-STY antibody confirms phosphorylation of the Nox1 peptide within the reaction mixture (FIG. 4F). These results provide direct evidence that PKC-βI phosphorylates Nox1 at T429.

T429 Phosphorylation Facilitates the Association of NoxA1 Activation Domain with Nox1

Figure 5:
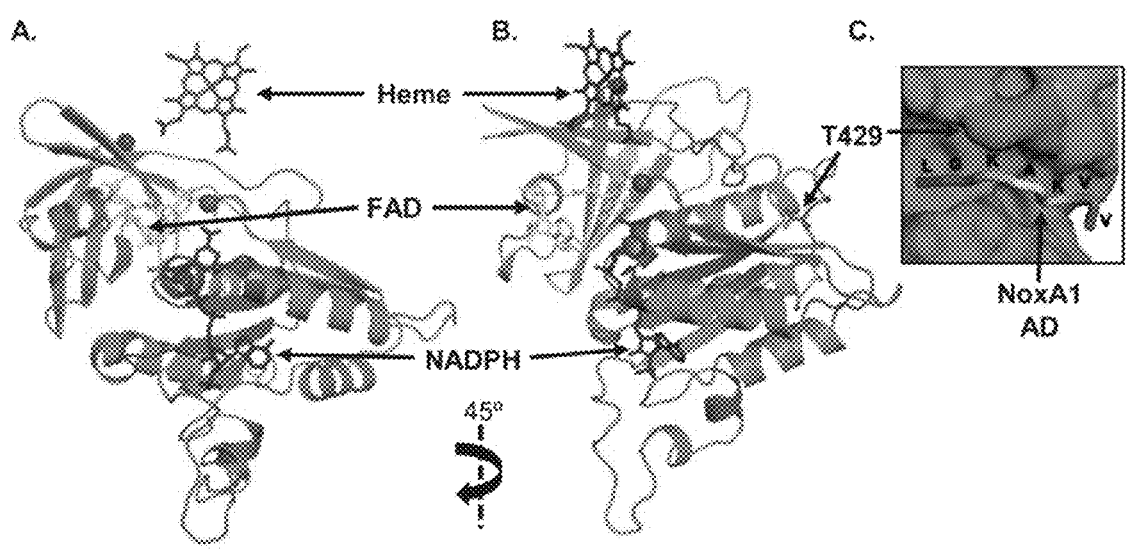
FIG. 5. Homology modeling of Nox1 cytosolic C-terminus and computational docking with NoxA1 activation domain. (A, B) Ribbon diagram of Nox1 C-terminus modeled based on the crystal structures of the FAD domain in cytochrome B5 reductase (PDB ID 2EIX) and the NADPH domain in Nox2 (PDB ID 3A1F) (SEQ ID NO:22). Cofactors within the Nox1 cytosolic C-terminus are noted by arrows. The N-terminus that attaches to the transmembrane domain is depicted as a blue sphere, and the extreme C-terminus of Nox1 is depicted as a red sphere. Residues involved in NADPH binding are depicted in blue, and residues involved in FAD binding are depicted in orange. The ribbon diagram in (B) is rotated 45° clockwise to reveal residues used to create the Nox1 peptide (purple), including T429. (C) Proposed interaction of the NoxA1 AD with Nox1 T429. The NoxA1 AD peptide (shown as the backbone with residues labeled) was computationally docked with the accessible surface area of Nox1 (modeled in green with T429 depicted in purple).

In response to various stimuli, the cytosolic subunit p47$^{phox}$ organizes the translocation and association of NoxA1 with the Nox1/p22$^{phox}$ complex at the membrane. This interaction involves the association of the NoxA1 activation domain (AD) with the C-terminus of Nox1 (Summito et al., 1994; Leto et al., 1994; Ambasta et al., 2006) though the mechanism is incompletely defined. Therefore, homology modeling was used to determine whether the position of T429 within the C-terminal domain might facilitate the interaction of Nox1 with cytosolic subunits. Using the cytochrome B5 reductase crystal structure for the FAD domain (PDB ID 2EIX) and the Nox2 crystal structure for the NADPH domain (PDB ID 3A1F) in the present model, T429 resides were found in an unstructured loop on the external surface of the Nox1 cytosolic domain (FIGS. 5A-B). The position of T429 suggested a potential interaction with NoxA1. The NoxA1 AD is also in an unstructured loop region as demonstrated by partial crystal structures of NoxA1 that contain the AD (Lapouge et al., 2000). Computational docking of the NoxA1 AD peptide with Nox1 consistently demonstrates its occupancy in a long groove near T429 (FIG. 5C). Based on these observations, it was hypothesized that phosphorylation of Nox1 at T429 is necessary for the interaction with NoxA1 AD.

Using peptides containing phosphorylated Nox1 at T429 (pNox1) and the NoxA1 AD, it was demonstrated by circular dichroism (CD) that these peptides are unstructured. Specifically, these peptides lack the characteristic peaks indicative of α-helices (positive at 190 nm, negative at 208 and 222 nm) and β-sheets (positive at 198 nm, negative at 215 nm, FIG. 6A). The presence of a negative peak below 200 nm, and positive (pNox1) or negative (NoxA1) shoulders at longer wavelengths (210-240 nm) demonstrate unstructured peptides. Furthermore, analysis of the complex of pNox1: NoxA1 peptides suggests subtle structural changes upon binding without evidence of secondary structure (FIG. 6A, inset).

Figure 6:
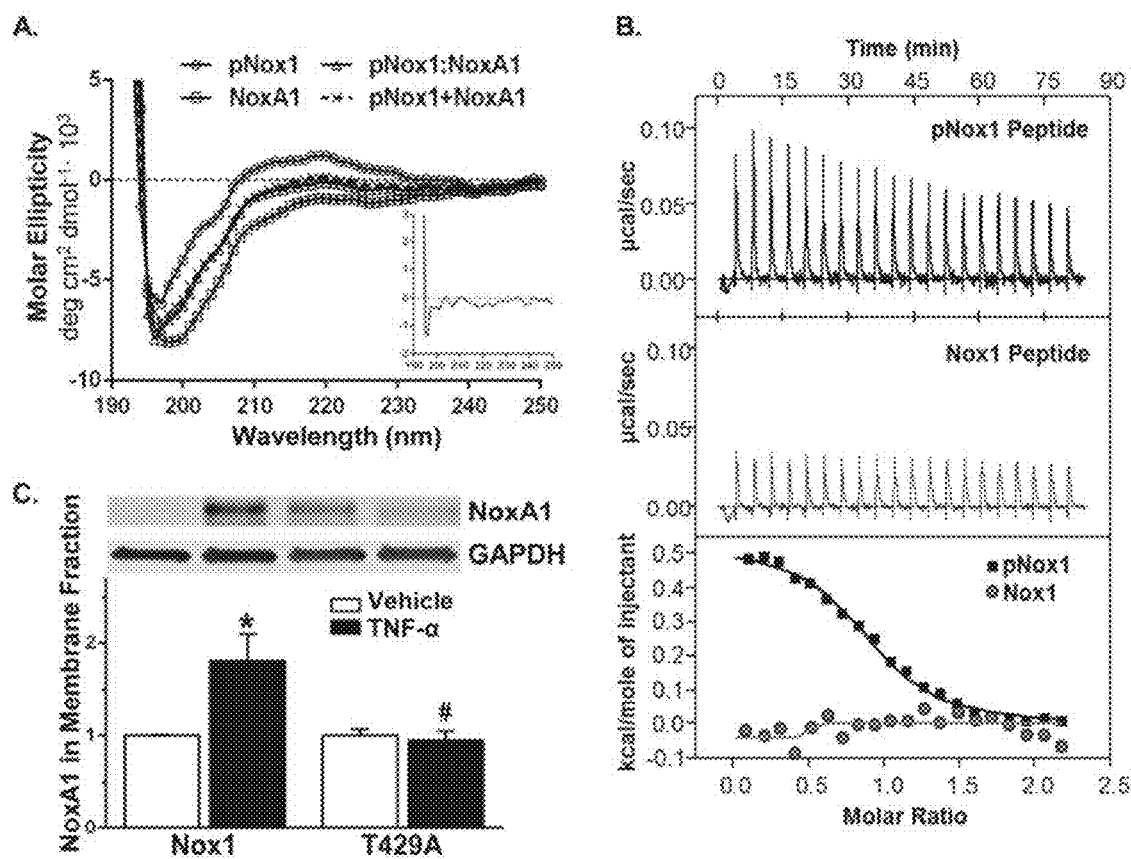
FIG. 6. Interaction of phosphorylated T429 of Nox1 with the NoxA1 activation domain is required for NoxA1 membrane recruitment. (A) Structural analysis of NoxA1 AD and phospho-Nox1 (pNox1) peptides by circular dichroism. Peptides for pNox1 and NoxA1 AD displayed characteristic random coil signals (negative dip below 200 nm and flat, near zero shoulders in the 210-220 nm range). Complex formation of the pNox1 peptide with NoxA1 AD peptide (pNox1:NoxA1) did not induce order and the circular dichroism signal is similar to that obtained by addition of the individual peptide signals (pNox1+NoxA1). Inset shows the residual curve of the pNox1:NoxA1 complex after subtraction of the individual components, indicating no major conformational changes of these peptides on complex formation. (B) Affinity and stoichiometry for the interaction of NoxA1 AD with pNox1 (top panel) and an unphosphorylated Nox1 peptide (middle panel) as measured by ITC. Lower panel, summary data. $K_d$>100 μM for unphosphorylated Nox1 peptide (stoichiometry N.D.) and 1.5±0.3 μM for pNox1 peptide (stoichiometry of 0.86±0.06; n=3 independent experiments). (C) Membrane recruitment of NoxA1 was assessed in CosPhox cells expressing p22$^{phox}$, NoxA1, and WT or T429A Nox1. After treating with TNF-α, membrane fractions isolated and blotted for NoxA1. Whole cell lysates (prior to membrane isolation) were probed with anti-GAPDH. n=4 independent experiments. *$p<0.05$ vs. Nox1 vehicle; #$p<0.05$ vs. Nox1 TNF-α-treated.

In order to determine whether Nox1AD directly interacts with Nox1 phosphorylated at T429, ITC was used to compare the affinity of the Nox1AD peptide with either the pNox1 peptide or a corresponding unphosphorylated Nox1 peptide (FIG. 6B). NoxA1 had no measurable interaction with the unphosphorylated Nox1 peptide (affinity >100 µM, stoichiometry N.D.), whereas its affinity for the pNox1 peptide was 1.5±0.3 µM at a stoichiometry of 0.86±0.06 (FIG. 6B, n=3). These results indicate that phosphorylation of T429 mediates the interaction with the activation domain of NoxA1.

Next, this interaction was validated in an intact biological system. NoxA1 localization to the membrane was assessed in cells expressing either WT or T429A Nox1. In CosPhox cells expressing p22$^{phox}$, p47$^{phox}$, and NoxA1, the expression of WT Nox1 resulted in the anticipated TNF-α-induced recruitment of NoxA1 to the membrane (FIG. 6C). By contrast, mutation of T429 prevented NoxA1 membrane translocation following TNF-α. As expected, WT but not T429A Nox1 caused a recruitment of p47$^{phox}$ to the membrane in response to TNF-α treatment (FIG. 13). These data provide additional support for NoxA1 binding to phosphorylated T429 Nox1 in the mechanism of NADPH oxidase activation.

DISCUSSION

Activation of Nox1 NADPH oxidase requires association with cytosolic proteins that function to organize the complex and activate the enzyme to produce superoxide. In this study, Nox1 activation was shown to be regulated by post-translational modification of the C-terminal region of Nox1. The present data demonstrate that phosphorylation of Nox1 at T429 by PKC-βI is necessary for TNF-α-mediated redox signaling and migration. Homology modeling combined with ITC revealed that Nox1 T429 phosphorylation facilitates association with the activation domain of NoxA1. Moreover, inhibition of T429 phosphorylation prevents recruitment of the cytosolic subunits to the membrane. Together with the observation that Nox1 is phosphorylated in multiple models of vascular disease, our findings suggest that strategies to inhibit Nox1 phosphorylation may mitigate its role in the pathogenesis of vascular disease.

Nox1 NADPH oxidase complex assembly is organized by p47$^{phox}$. The phosphoinositide-binding (PX) domain of p47$^{phox}$ mediates membrane association, the Src homology 3 (SH3) domains interact with p22$^{phox}$, and the proline rich (PR) domain interacts with the SH3 domain of NoxA1 or p67$^{phox}$ (Ago et al., 2003; Groemping et al., 2003) p47$^{phox}$ and NoxA1 associate in the cytosol under basal conditions. Phosphorylation of p47$^{phox}$ releases binding of an auto-inhibitory domain, (Sumimoto et al., 1994; Huang et al., 1999; Ago et al., 2003) allowing translocation of the p47$^{phox}$/NoxA1 complex to the Nox1/p22$^{phox}$ complex, positioning the NoxA1 AD with the C-terminus of Nox1 (Sumimoto et al., 1994; Leto et al., 1994; Ambasta et al., 2006). NoxO1, a homolog of p47$^{phox}$ lacking the auto-inhibitory domain, appears to colocalize with Nox1 in resting cells at the membrane via its PX domain (Dehbabi et al., 2013; Cheng et al., 2004). Phosphorylation of each of the cytosolic subunits has been implicated in regulating complex assembly (Debbabi et al., 2013; Benna et al., 1997; Kroviarski et al., 2010).

In contrast to the cytosolic subunits, less is known regarding phosphorylation of the catalytic subunits. The present study provides the first evidence for the phosphorylation of Nox1. The Nox2 C-terminal domain (within residues 321-405 and 466-570) has recently been shown to be phosphorylated at serine and threonine residues (Raad et al., 2009). Similar to Nox1, phosphorylation of Nox2 was associated with increased ROS production and complex assembly in response to agents that stimulate PKC. However, there appears to be important differences in phosphorylation-mediated activation of Nox1 and Nox2. First, despite significant homology in surrounding residues, the T429 was shown to be phosphorylated on Nox1 and is not conserved in Nox2. Second, although the specific residue phosphorylated on Nox2 was not identified, Ser333, Thr509, and Ser550 are the most likely phosphorylation sites. Interestingly, Ser333 and Thr509, but not Ser550, are conserved between Nox2 and Nox1. Third, phosphorylation of Nox5 in the FAD domain (T494/5498) has also been shown to regulates its activity (Jagnandan et al., 2007). Although the mechanism is not clear, it will be distinct from that of Nox1 and Nox2 since Nox5 does not require complex assembly for activation.

Nox1 activation is important in mediating multiple cellular pathways involved in the pathogenesis of vascular disease (Lessegal et al., 2012). The present data demonstrate that migration of cultured VSMCs to TNF-α requires Nox1. Cell migration is also regulated by the PKC family of serine/threonine kinases that include PKC-βI, (Housey et al., 1988; Debbabi et al., 2013; Garcia et al., 1988; Ahmed et al., 1998; Dusi et al., 1993; Forbes et al., 1999; Lewis et al., 2011). suggesting a functional link between Nox1 activation and PKC phosphorylation. Providing direct evidence for PKC-βI phosphorylation of Nox1, recombinant PKC-βI was found to phosphorylates a Nox1 peptide containing T429 in vitro. Moreover, loss of Nox1 phosphorylation at T429 or the knock down of PKC-βI is sufficient to inhibit ROS production and cell migration. In contrast, the knock down of PKC-βI only partially inhibited TNF-α-induced Nox1 phosphorylation, indicative of phosphorylation of Nox1 by other kinases. In support of this interpretation, Nox1 contains residues that are homologous with proposed Nox2 phosphorylation sites (Raad et al., 2009).

Until now, the molecular mechanism whereby Nox1 interacts with the NoxA1 AD was not known. Using ITC, evidence is provided herein that phosphorylation of Nox1 T429 increases the association of this region to the NoxA1 AD by more than a hundred-fold. Furthermore, the T429A mutant is not able to sustain association of the p47phox/NoxA1 complex with the Nox1/p22phox complex. Assembly of NoxA1 to Nox1 may position its activation domain within a long groove adjacent to the T429 of Nox1. Taken together, the present data suggest that a negative change associated with phosphorylation at T429 is the principle mechanism that stabilizes NoxA1 with the membrane complex.

In conclusion, in response to TNF-α, Nox1 requires phosphorylation at T429 for complex assembly, ROS generation and VSMC migration. The data support a mechanism by which PKC-βI phosphorylation of Nox1 T429 facilitates interaction and stabilization of the NoxA1 AD with Nox1. Furthermore, this provides the first computational model of the Nox1 C-terminus and propose that the NoxA1 AD is positioned in a long groove near T429. In combination with the findings that Nox1 is phosphorylated in atherosclerosis, VSMC dedifferentiation, and neointimal formation, phosphorylation of Nox1 was identified as a new target for effective and directed therapy of vascular disease.

REFERENCES

Ago et al., *Proceedings of the National Academy of Sciences of the United States of America*, 100:4474 (2003).
Ahmed et al., *J. Biol. Chem.*, 273:15693 (1998).
Ambasta et al., *Free Radical Biology & Medicine*, 41:193 (2006).
Banfi et al., *J. Biol. Chem.*, 278:3510 (2003).
Benna et al., *J. Biol. Chem.*, 272:17204 (1997).
Carter et al., *Antioxid Redox Signal*, 11:1569 (2009).
Chen et al., *The Journal of Biological Chemistry*, 281:21183 (2006).
Cheng and Lambeth, *J. Biol. Chem.*, 279:4737 (2004).
Chu et al., *Arteriosclerosis, Thrombosis, and Vascular Biology*, 31:345 (2011).
Dassie et al., *Nat. Biotech.*, 27:839 (2009).
Debbabi et al., *Faseb J.*, (2013).
Debbabi et al., *Faseb J.*, 27:1733 (2013).
Dusi and Rossi, *Biochem. J.*, 296(Pt 2):367 (1993).
Forbes et al., *Biochem. J.*, 338(Pt 1):99 (1999).
Fukui et al., *Biochimica Et Biophysica ACTA*, 1231:215 (1995).
Garcia et al., *Biochem. J.*, 252:901 (1988).
Groemping et al., *Cell*, 113:343 (2003).
Hanna et al., *Free Radical Biology & Medicine*, 37:1542 (2004).
Harraz et al., *J. Clin. Invest.*, 2008; 118:659-670
Housey et al., *Adv. Exp. Med. Biol.*, 234:127 (1988).
Huang and Kleinberg, *J. Biol. Chem.*, 274:19731 (1999).
Jagadeesha et al., *Cardiovasc. Res.*, 93:406 (2012).
Jagnandan et al., *J. Biol. Chem.*, 282:6494 (2007).
Kawahara et al., *J. Biol. Chem.*, 280:31859 (2005).
Kim et al., *The Journal of Biological Chemistry*, 282:34787 (2007).
Kim et al., *Nucl. Acid. Thera.*, 21:173 (2011).
Kobayashi et al., *Biochem. Biophys. Res. Commun.*, 159:548 (1989).
Kroviarski et al., *Faseb J.*, 24:2077 (2010).
Kubo et al., *FEBS Letters*, 223:138 (1987).
Lambeth, *Nat. Rev. Immunol.*, 4:181 (2004).
Lapouge et al., *Mol. Cell*, 6:899 (2000).
Lassegue et al., *Circ. Res.*, 110:1364 (2012).
Lee et al., *Arterioscler. Thromb. Vasc. Biol.*, 29:480 (2009).
Leto and Geiszt, *Antioxid Redox Signal*, 8:1549 (2006).
Leto et al., *Proc. Natl. Acad. Sci. U.S.A.*, 91:10650 (1994).
Lewis et al., *The Journal of Biological Chemistry*, 285:2959 (2010).
Lim et al., *Prostate*, 62:200 (2005).
Maehara et al., *J. Biol. Chem.*, 285:31435 (2010).
Marden et al., *The Journal of Clinical Investigation*, 117:2913 (2007).
Miller et al., *Antioxidants & Redox Signaling*, 12:583 (2010).
Miller et al., *Circulation Research*, 101:663 (2007).
Morris et al., *J. Comput. Chem.*, 19:1639 (1998).
O'Leary et al., *PLoS One*, 7:e44176 (2012).
Price et al., *Blood*, 99:2653 (2002).
Raad et al., *Faseb J.*, 23:1011 (2009).
Raad et al., *Faseb J.*, 23:1011 (2009).
Reinehr et al., *Glia*, 55:758 (2007).
Riboldi et al., *Prog. Neurobiol.*, 95:133 (2011).
Rockey et al., *Nucl. Acid Thera.*, 21:299 (2011).
Rokutan et al., *Antioxid Redox Signal*, 8:1573 (2006).
Rokutan et al., *Semin Immunopathol.*, 30:315 (2008).
Schroder et al., *Arterioscler. Thromb. Vasc. Biol.*, 27:1736 (2007).
Stanic et al., *Arterioscler. Thromb. Vasc. Biol.*, 32:2452 (2012).
Streeter et al., *Cardiovasc. Ther.*, (2012).
Sumimoto et al., *Proceedings of the National Academy of Sciences of the United States of America*, 91:5345 (1994).
Thiel et al., *NAR*, 40:6319 (2012).
Thiel et al., *PLOS ONE*, 7:e43836 (2012).
Todd and Gomez, *Anal. Biochem.*, 296:179 (2001).
Tominaga et al., *Free Radic. Biol. Med.*, 43:1627 (2007).
Ueyama et al., *Mol. Cell Biol.*, 26:2160 (2006).
Xu et al., *J. Vasc. Res.*, 49:242 (2012).
Zhang et al., *Blood*, 116:1377 (2010).
Zimmerman et al., *Hypertension*, 58:446 (2011).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A pharmaceutical composition comprising an effective amount of an isolated peptide or fusion protein comprising the peptide, wherein the peptide has formula (I):

$$Z_1-X_1-X_2-X_1-X_3-X_1-X_1-X_2-Y-F-Z_1 \quad \text{(SEQ ID NO: 11)}$$

wherein each $X_1$ is independently K, N, Q, or H;
wherein each $X_2$ is independently L, I, A, G or V;
wherein $X_3$ is T, S, Y, D, or E; and
wherein each $Z_1$ is independently absent, or is 1 to 50 amino acids in length; and a pharmaceutically acceptable vehicle, wherein the isolated peptide or fusion protein is no more than 100 amino acids in length.

2. The composition of claim 1 wherein in formula (I) $X_3$ is T.

3. The composition of claim 1 wherein the peptide or fusion protein is no more than 50 amino acids in length.

4. The composition of claim 1 wherein the peptide or fusion protein is no more than 20 amino acids in length.

5. The composition of claim 1 wherein the fusion protein comprises a targeting peptide.

6. The composition of claim 5 wherein the targeting peptide provides for cell membrane and/or nuclear membrane transport.

7. The composition of claim 6 wherein the targeting peptide is RrRK, RKKRRQRRR (SEQ ID NO:23), CGNKRTRGC (SEQ ID NO:24), Oct4PTD or penetratin.

8. The composition of claim 1 wherein the fusion protein comprises a peptide sequence that is a protease cleavage site.

9. The composition of claim 1 which is incorporated into a liposome.

10. The composition of claim 1 wherein $X_3$ is phosphorylated.

11. The composition of claim 1 wherein the peptide has KLKTQKIYF (SEQ ID NO:9).

* * * * *

UNITED STATES PATENT AND TRADEMARK OFFICE
CERTIFICATE OF CORRECTION

PATENT NO. : 9,951,102 B2
APPLICATION NO. : 14/689803
DATED : April 24, 2018
INVENTOR(S) : Miller, Jr. et al.

It is certified that error appears in the above-identified patent and that said Letters Patent is hereby corrected as shown below:

On the Title Page

In item (*), in "Notice", in Column 1, Line 3, delete "days. days." and insert --days.-- therefor In Column 2, item (56) under "Other Publications", Line 27, delete "Selectrion"," and insert --Selection",-- therefor In item (57), in "Abstract", in Column 2, Line 4, delete "p47phox/NoxA1" and insert --p47$^{phox}$/NoxA1-- therefor In the Specification In Column 1, Line 43, delete "NoxO1" and insert --NoxA1-- therefor In Column 1, Line 66, delete "p47phox/NoxA1" and insert --p47$^{phox}$/NoxA1-- therefor In Column 2, Line 23, delete "p47phox/NoxA1" and insert --p47$^{phox}$/NoxA1 -- therefor In Column 2, Line 24, delete "PKC-β1" and insert --PKC-βI-- therefor In Column 3, Line 9, delete "F-Z1(SEQ ID NO: 1)," and insert --F-Z1 (SEQ ID NO:11),-- therefor In Column 3, Line 24, delete "absent;" and insert --absent,-- therefor In Column 3, Line 27, delete "embodiment;" and insert --embodiment,-- therefor In Column 3, Lines 63-64, delete "p47phox/NoxA1" and insert --p47$^{phox}$/NoxA1-- therefor In Column 5, Line 42, delete "PKC-β1" and insert --PKC-βI-- therefor Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,951,102 B2

In Column 5, Line 43, delete "TNT-α-induced" and insert --TNF-α-induced-- therefor In Column 5, Line 52, delete "TNT-α-stimulated" and insert --TNF-α-stimulated-- therefor In Column 5, Line 56, delete "NO:9." and insert --NO:9,-- therefor In Column 16, Line 47, delete "p47phox/NoxA1" and insert --p47$^{phox}$/NoxA1-- therefor In Column 16, Lines 52-53, delete "α,α-disubstituted" and insert --α, α-disubstituted-- therefor In Column 23, Line 26, delete "μl" and insert --μL-- therefor In Column 24, Line 54, delete "DH5a" and insert --DH5α-- therefor In Column 25, Line 12, delete "μl" and insert --μL-- therefor In Column 26, Line 5, delete "μL," and insert --μL-- therefor In Column 26, Line 8, delete "μL," and insert --μL-- therefor In Column 26, Line 9, delete "μL," and insert --μL-- therefor In Column 26, Line 11, delete "μL," and insert --μL-- therefor In Column 26, Line 11, delete "μL," and insert --μL-- therefor In Column 26, Line 14, delete "μL," and insert --μL-- therefor In Column 26, Line 20, delete "hm_build.mer" and insert --hm_build.mcr-- therefor In Column 26, Line 21, delete "13.1.5" and insert --13.1.25-- therefor In Column 26, Line 24, delete "(PUB" and insert --(PDB-- therefor In Column 26, Line 32, delete "(Schrödinger)," and insert --(Schrödinger).-- therefor In Column 27, Line 5, delete "C-131" and insert --C-βI-- therefor In Column 30, Line 5, delete "NoxO1," and insert --NoxA1,-- therefor In Column 30, Line 30, delete "(T494/5498)" and insert --(T494/S498)-- therefor In Column 30, Lines 60-61, delete "p47phox/NoxA1" and insert --p47$^{phox}$/NoxA1-- therefor In Column 30, Line 61, delete "Nox1/p22phox" and insert --Nox1/p22$^{phox}$-- therefor

CERTIFICATE OF CORRECTION (continued)
U.S. Pat. No. 9,951,102 B2

In the Claims

In Column 47, Line 54, in Claim 1, after "and", insert --¶--

In Column 48, Line 47, in Claim 6, delete "and/or" and insert --or-- therefor

In Column 48, Lines 50-51, in Claim 7, delete "CGNKR.TRGC (SEQ 11)" and insert --CGNKRTRGC (SEQ ID-- therefor